United States Patent [19]

Melaja et al.

[11] 4,008,285
[45] Feb. 15, 1977

[54] PROCESS FOR MAKING XYLITOL

[76] Inventors: Asko J. Melaja, Niittypolku 6, Kantvik; Lauri Hämäläinen, Rajakallio C, 02460 Kantvik, both of Finland

[22] Filed: June 18, 1975

[21] Appl. No.: 588,022

Related U.S. Application Data

[60] Division of Ser. No. 463,037, April 22, 1974, abandoned, which is a continuation-in-part of Ser. No. 354,391, April 25, 1973, abandoned.

[52] U.S. Cl. .............................. 260/635 C; 127/37; 127/46 A; 127/46 B; 260/637 R; 536/1
[51] Int. Cl.² ................... C07C 31/18; C13K 13/00
[58] Field of Search ................. 127/37, 46 R, 46 A, 127/46 B; 260/635 C, 635 R, 637 R

[56] References Cited

UNITED STATES PATENTS

| | | | |
|---|---|---|---|
| 2,818,851 | 1/1958 | Khym | 127/55 |
| 2,890,972 | 6/1959 | Wheaton | 127/46 B |
| 2,917,390 | 12/1959 | Apel | 260/635 C |
| 3,305,395 | 2/1967 | Scallet | 127/46 B |
| 3,420,709 | 1/1969 | Barrett | 127/53 |
| 3,558,725 | 1/1971 | Kohno | 260/635 C |
| 3,579,380 | 5/1971 | Friese | 260/635 C |
| 3,784,408 | 1/1974 | Jaffe | 260/635 C |
| 3,830,770 | 5/1973 | Zievers | 127/46 A |

OTHER PUBLICATIONS

O. Samuelson et al., Actd. Chem. Scand., 22, 1252–1258 (1968).

Primary Examiner—Morris O. Wolk
Assistant Examiner—Sidney Marantz
Attorney, Agent, or Firm—Brumbaugh, Graves, Donohue & Raymond

[57] ABSTRACT

A method for recovering xylitol from pentosan-, preferably xylan-containing raw materials including the steps of hydrolyzing the raw material, purifying the hydrolysate by ion exclusion and color removal, and then subjecting the purified solution to chromatographic fractionation to provide a solution containing a high level of xylose. The xylose solution is hydrogenated and a xylitol-rich solution is recovered by chromatographic fractionation using ion exchange resins.

16 Claims, 15 Drawing Figures

FIG. 2 FOUR PROCEDURES FOR PENTOSE SUGAR SOLUTION FINAL PURIFICATION AND COLOR REMOVAL

CHROMATOGRAPHIC FRACTIONATION AND CRYSTALLIZATION OF XYLITOL

SEPARATION OF POLYOLS
Resin in Al$^{+++}$- form
(rate 3.2 ml/min)

SEPARATION OF POLYOLS
Resin in $Al^{+++}$-form
(rate 2.2 ml/min)

SINGLE FRACTIONATION

DOUBLE FRACTIONATION

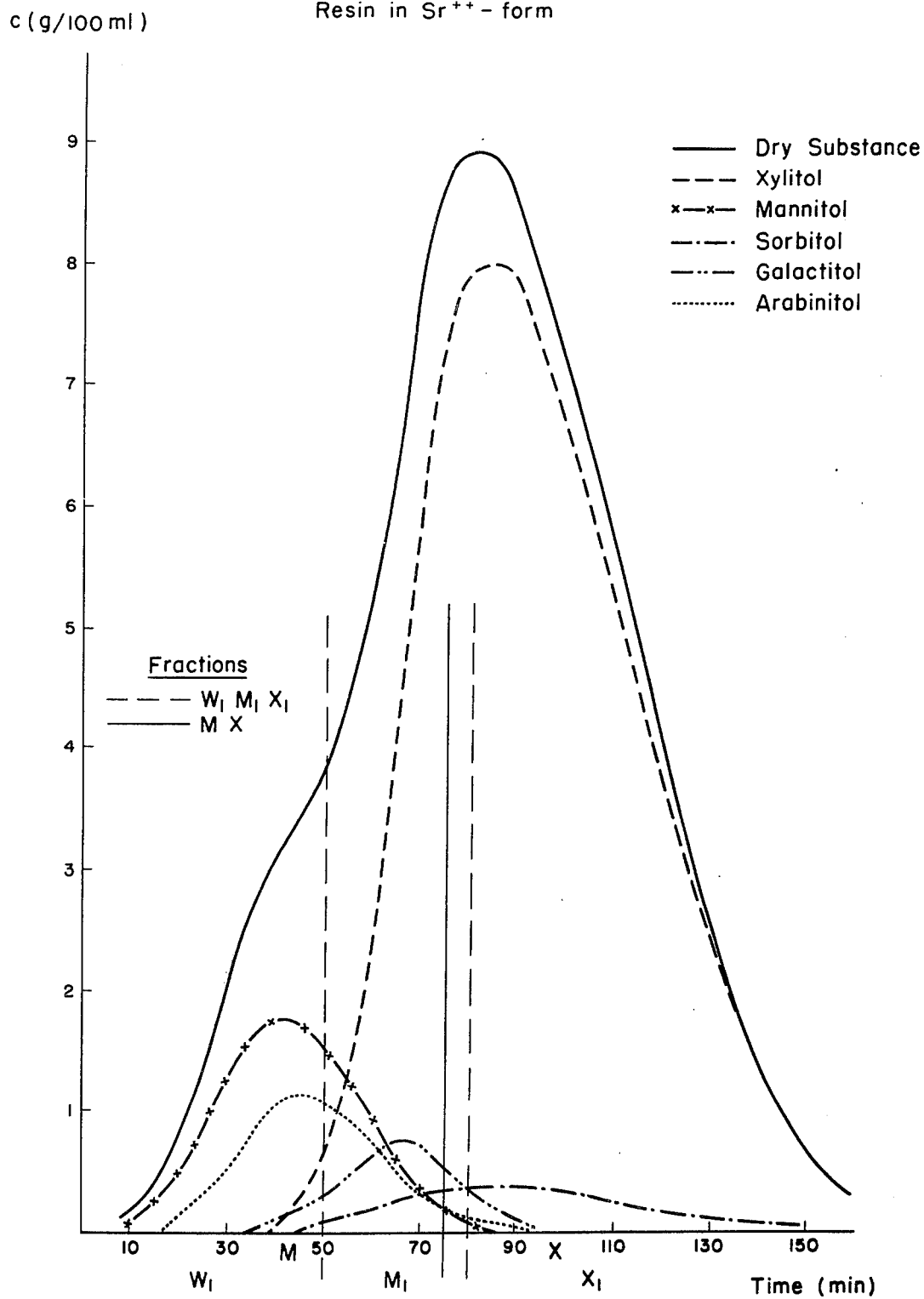

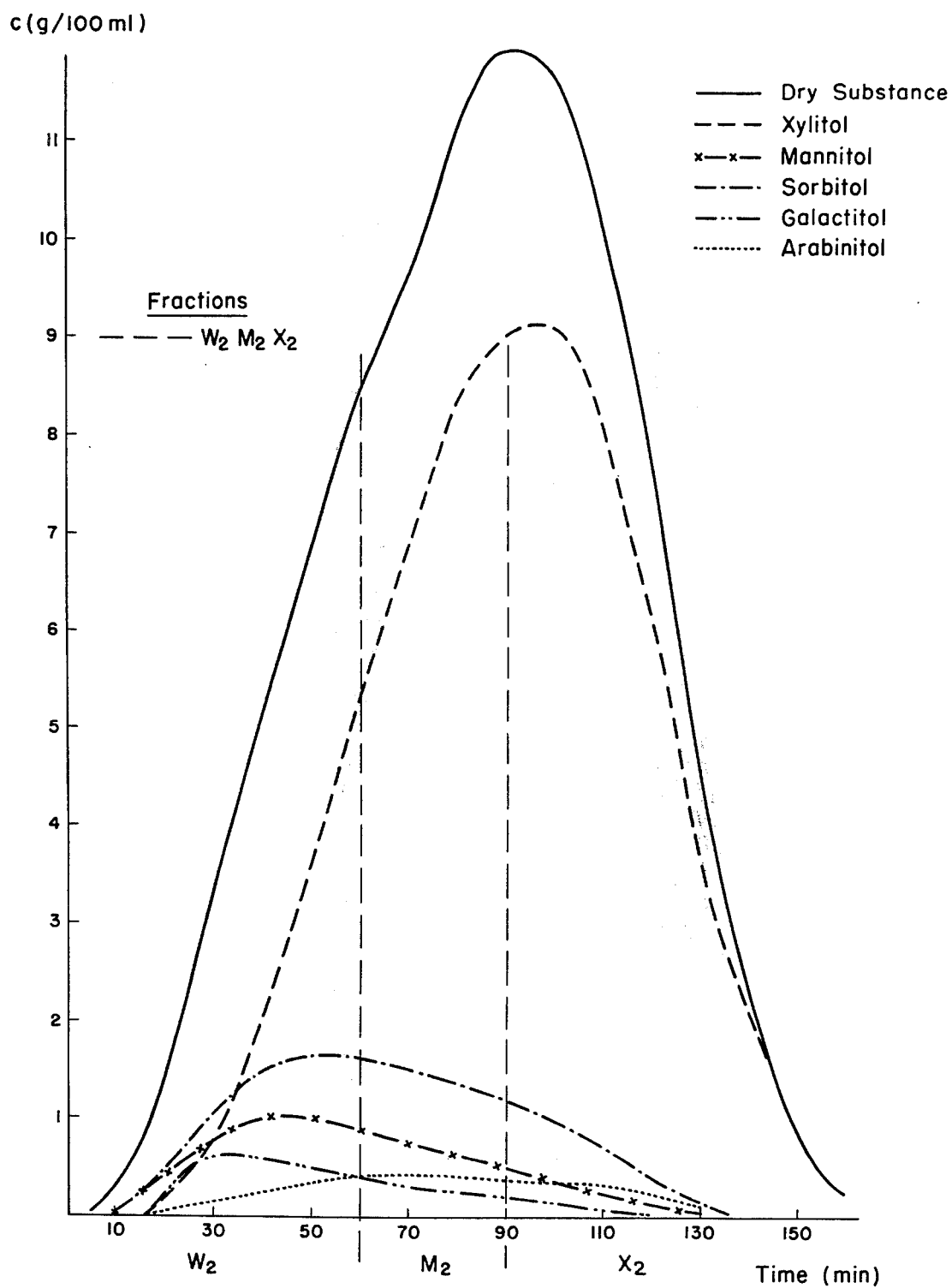

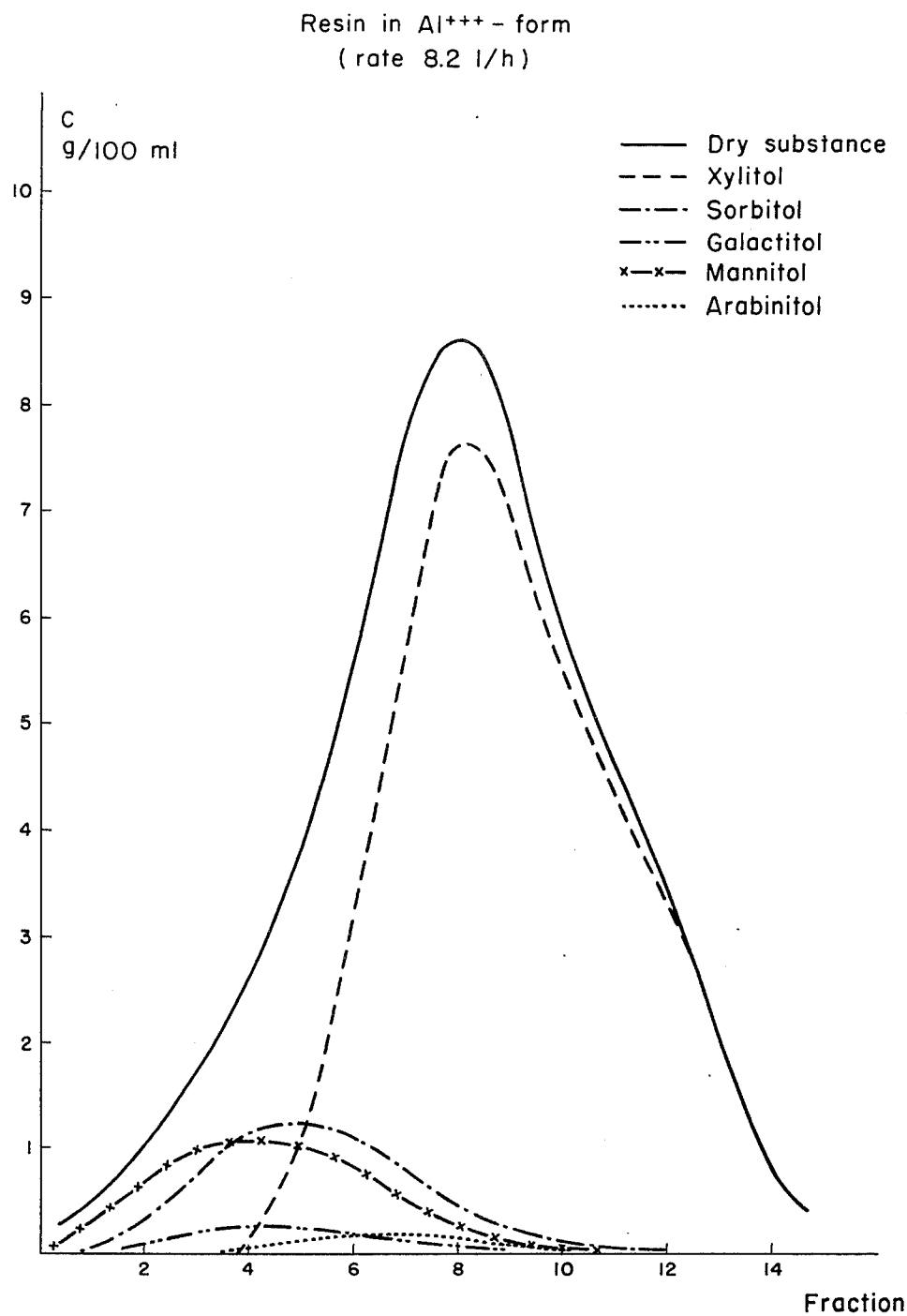

PROCESS FOR MAKING XYLITOL

This is a division, of application Ser. No. 463,037, filed Apr. 22, 1974, now abandoned, which is a continuation-in-part of application Ser. No. 354,391, filed Apr. 25, 1973, now abandoned.

This invention relates to a process for obtaining xylitol from pentosan-containing materials, preferably xylan-containing materials by acid hydrolysis of the materials followed by purifying and chromatographic separation techniques.

The prior art is replete with processes described as being suitable for obtaining xylose and/or xylitol from natural products such as birch wood, corn cobs, cotton seed hulls and the like. The Russian article by Leihin, E. R. and Soboleva, G. D., Proizvostro Ksilita (Production of Xylitol) Moscow, 1962 gives a review of the processes known at that time.

Recent United States patents dealing with the subject include U.S. Pat. Nos. 3,212,932 and 3,558,725. British Patent No. 1,209,960 and Russian Patent No. 167,845, 1965, contain related disclosure.

The prior art processes have not been employed to any great extent on a commercial scale because they are economically unsound. For example, where the xyloserich solutions are obtained from wood chips following the prior art processes, the solutions have been so impure that several costly process steps, are required before xylose can be recovered or before a solution of appropriate purity is obtained that can be hydrogenated to form xylitol.

In accordance with the present invention, an improved method for the production of xylitol from pentosan-containing, specifically xylan-containing raw materials has now been developed in which a pentose-rich solution obtained by acid hydrolysis of a pentosan containing raw material is purified by mechanical filtration and ion exclusion techniques for color removal and desalting. This solution is then subjected to chromatographic fractionation to obtain a highly purified solution of xylose. The xylose solution of high purity may be used as a source of xylose in aqueous solution form, or xylose may be crystallized therefrom. The next step in the process is hydrogenating the solution to produce xylitol. Pure xylitol is then recovered from the reaction mixture by chromatographic fractionation. In both this and the earlier stage of the process, a preferred way of accomplishing the chromatographic fractionation step is by passing the solution through a column of an alkaline earth metal salt of a polystyrene sulfonate cation exchange resin cross-coupled with di-vinyl benzene, the column having a height of from about 2.5 to about 5 meters. In another preferred manner of separating the polyols and recovering pure xylitol, trivalent metal salts, such as $Fe^{+++}$ and $Al^{+++}$, of a polystyrene sulfonate cation exchange resin cross-coupled with di-vinyl benzene are used in the chomatographic fractionation step.

One of the advantages of the process of this invention is that it provides a solution of xylose of sufficiently high purity to warrant hydrogenation thereof to xylitol on a commercial scale if desired.

Materials used as the raw materials from which the pentosan-rich solutions are obtained are preferably lignocellulose materials including wood of various species of trees, such as birch and beach. Also useful are oat hulls, corn cobs and stalks, coconut shells, almond shells, straw, bagasse and cotton seed hulls, Where wood is used, it is preferably subdivided into wood chips, shavings, saw dust and the like.

DESCRIPTION OF THE DRAWINGS

The invention will be further described with reference to the drawings, in which:

FIG. 13 is graph showing distribution of various polyols in successive fractions taken during the first fractionation of Example XIV, using the $Sr^{+++}$ form of resin;

FIG. 14 is a graph showing distribution of various polyols in successive fractions taken during the second fractionation of the solution of polyols described in Example XIV, using the $Fe^{+++}$ form of resin; and FIG. 15 is a graph showing the results of the polyol separation described in Example XV.

Referring to FIG. 1, the raw materials may be hydrolyzed in the first stage of the present invention by following any of the well known procedures in the art. Suitable procedures described in the literature include those given in U.S. Pat. Nos. 2,734,836; 2,759,856; 2,801,939; 2,974,067 and 3,212,932. The important considerations in selecting the appropriate method of hydrolysis is that a maximimum yield of pentoses be obtained and that the resulting pentose-rich solution be neutralized using materials which do not cause serious deterioration of sugars, such as sodium hydroxide. Where the pentose material is obtained by methods other than acid hydrolysis, the step of desalting by ion exclusion described below may not be required.

The next stage in the process where a hydrolysis product is used is that of the purification of the hydrolysis product. The purification stage comprises two main steps; one is removal of the salt, sodium sulfate, and the major part of organic impurities and coloring bodies by ion-exclusion techniques, while the second step accomplishes final color removal. The ion exclusion technique removes salt from the solution and similar processes have been used in the sugar industry for the purification of molasses. Suitable processes are described for example in U.S. Pat. Nos. 2,890,972 and 2,937,959.

Upon completion of the salt removal step the solution still contains some organic and inorganic impurities. These are removed by the color removal step by treating the impure solutions with ion exchange systems consisting of a strong cation exchanger followed by a weak anion exchanger and then followed by a step of passing the solution through an adsorbant or activated carbon bed. These methods are also known in the sugar industry. One such procedure is described for example in U.S. Pat. No. 3,558,725. Other pertinent disclosures of this feature include J. Stamberg and V. Valter: Entfarbungsharze, Akademie Verlag Berlin 1970; P. Smit: Ionenaustauscher und Adsorber bei der Herstellung und Reinigung von Zuckern, Pektinen und verwandten Stoffen. Akademie Verlag Berlin 1969; J. Hassler: Activated carbon; Leonard Hill London 1967.

Figure 2:
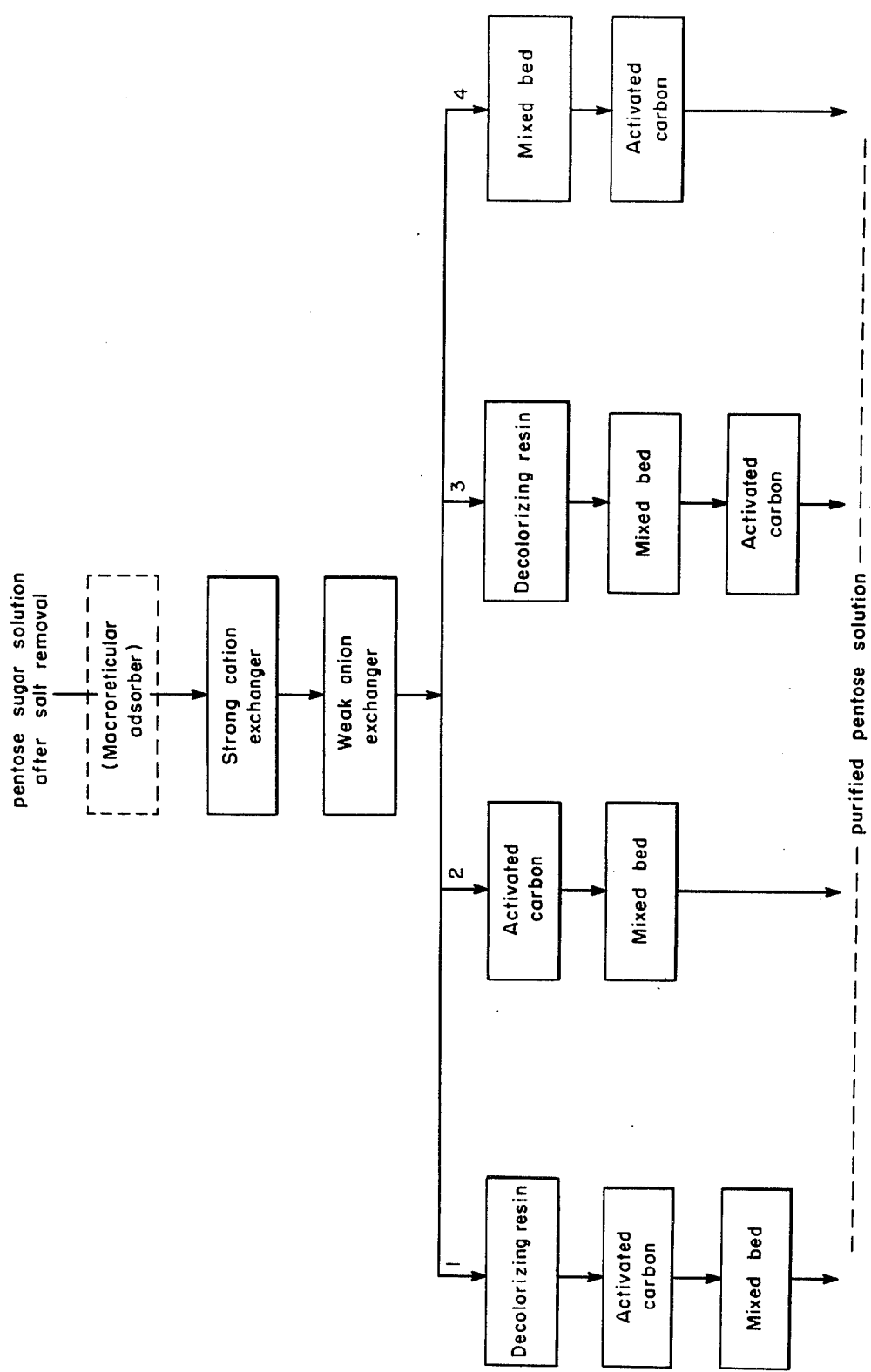
FIG. 2 is a flow diagram showing four possible procedures for purifying pentose sugar solutions in accordance with the invention.

As shown in FIG. 2 the purification step may be further improved where necessary by the addition of a step which uses a synthetic macroreticular adsorbant such as Amberlite XAD 2 to remove organic impurities. The macroreticular adsorbant can be used in the purification stage immediately following the ion exclusion step but prior to the cation exchanger as shown in FIG. 2. Altenatively, it can be the final step of the purification stage.

FIG. 2 shows four alternate schemes for accomplishing the purification stage of the process of the present invention. Selection of one of these alternate schemes will depend upon the nature and level of the impurities present in the solution and upon the composition of the solution undergoing purification.

Figure 1:
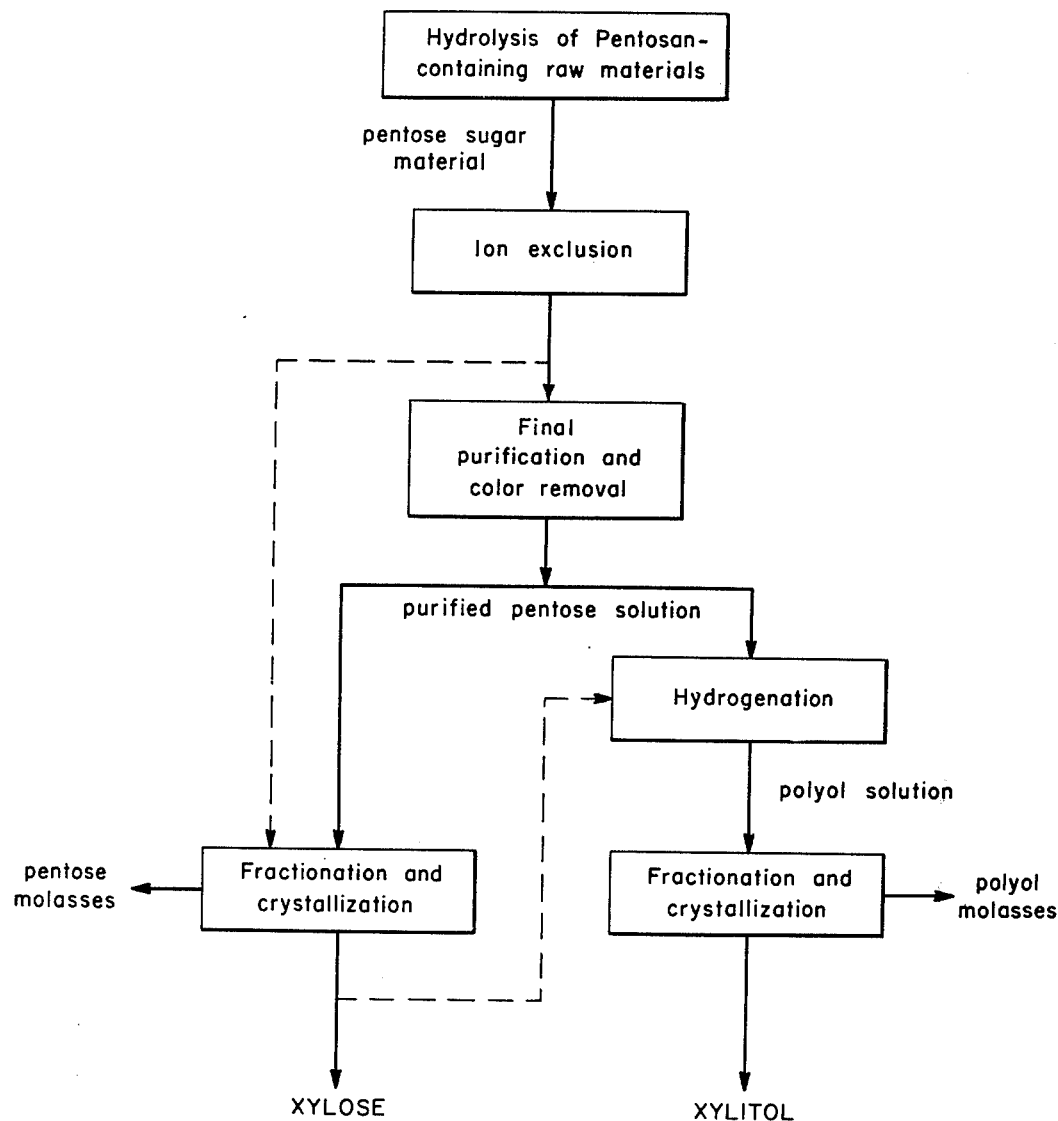
FIG. 1 is a flow diagram showing generally the processes of the present invention.

The purified pentose solution obtained in the purification stage may then be used for the recovery of xylose as shown in FIG. 1 by chromatographic fractionation to obtain a solution with a high purity with respect to xylose, followed by crystallization. The pentose molasses, made up of unselected fractions, may be subjected to further chromatographic fractionation procedures to recover one or more of the other sugars present therein. Alternatively, it can be used as a source of carbohydrate in fermentation processes.

Figure 3:
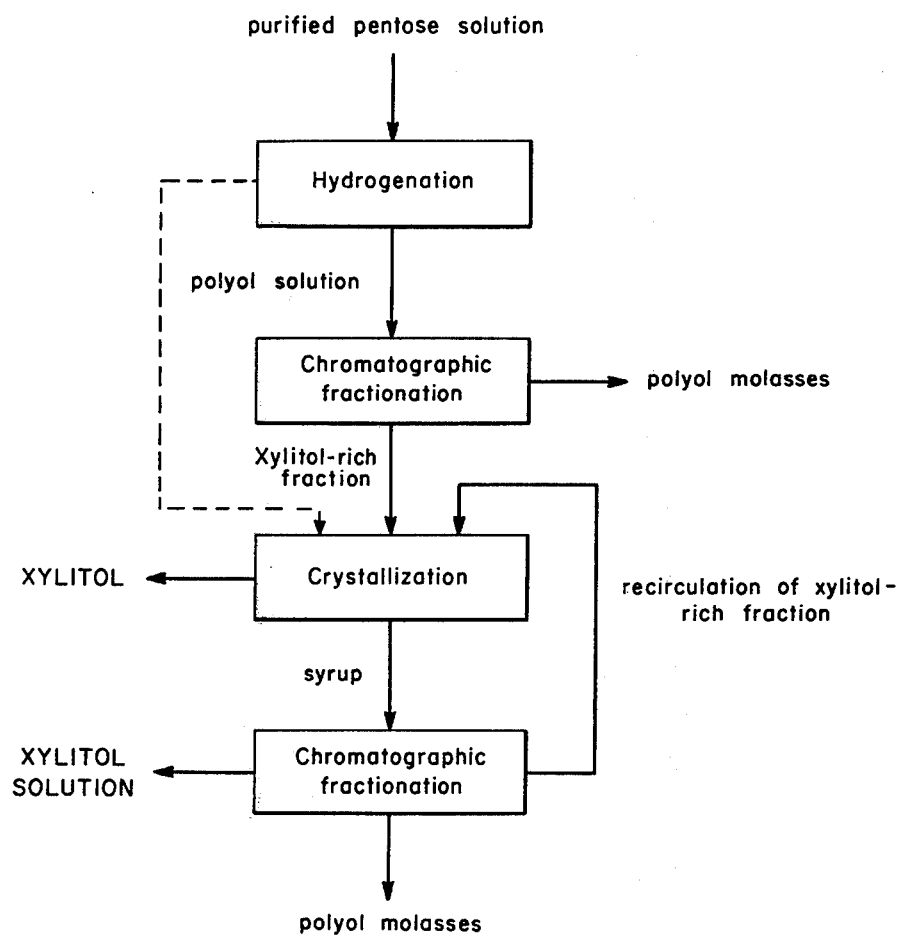
FIG. 3 is a flow diagram disclosing the procedure whereby xylitol is recovered from a hydrogenated pentose solution.

Alternatively, where xylitol is desired, the purified pentose solution is hydrogenated and treated according to the procedure outlined in FIG. 3. The hydrogenation process is conducted in a manner similar to the hydrogenation of glucose to sorbitol. A suitable process is found in an article by W. Schnyder entitled "The Hydrogenation of Glucose to Sorbitol with Raney Nickel Catalyst," Dissertation at the Polytechnical Institute of Brooklyn, 1962.

It has additionally been found that unhydrogenated sugars present in the hydrogenated pentose solution are easily separated from the mixture of polyols by following ion-exchange chromatographic techniques. The unhydrogenated sugars are eluted from the column ahead of the polyols. The fractions shown in FIGS. 5 and 6 as "unknown impurities" were found to contain substantial quantities of unhydrogenated sugars. Thus, the process of the present invention provides a method of obtaining pure polyols, even though hydrogenation is incomplete and permits the use of continuous hydrogenation method, if desired.

The ion exchange resins used in separating the polyols in accordance with this invention are of the type described as sulfonated polystyrene cation exchange resins cross coupled with di-vinyl benzene. The alkaline earth metal salts of these resins, such as the calcium, barium and strontium form provide acceptable results and of these the strontium form gives the best separation of the polyols. A significant improvement in the separation of certain polyols is obtained where the trivalent metal forms such as the $Al^{+++}$ and $Fe^{+++}$ are used. It has been found for example that the $Al^{+++}$ and $Fe^{+++}$ forms of the resin provide at least three advantages over the use of the alkaline earth metal forms by themselves. In the first place, it has been found that the polyols are eluted from the $Al^{+++}$ and $Fe^{+++}$ in a different order. This was surprising and is important because separation of the major impurity, sorbitol, is thus improved.

In the second place, in the recovery of xylitol it is possible to avoid the accumulation of sorbitol caused by recycling by either carrying out the fractionation initially on a resin of either $Al^{+++}$ or $Fe^{+++}$ form or by using a double fractionation process where a first fractionation is conducted on a resin in alkaline earth metal form followed by a second fractionation on a resin in $Al^{+++}$ or $Fe^{+++}$ form.

As a third advantage, it is possible to advantageously separate any desired polyol from a mixture of polyols resulting from the hydrogenation of wood hydrolysates.

EXAMPLE I

As an example of the hydrogenation step conducted in accordance with the process of the present invention, a suitable feed solution obtained by purification of a birch wood hydrosylate is subjected to catalytic hydrogenation to form a xylitol-rich solution. The feed solution in the amount of 1,500 grams having a concentration of solids of 50% by weight and the solids comprising 75% xylose and 25% other sugars is hydrogenated in a batch autoclave using a Raney nickel catalyst at a temperature of 135° C for 2½ hours, at a hydrogen pressure of 40 atmospheres. At the end of this time the catalyst is removed by filtration and and residual amount of nickel remaining in the solution is removed by ion exchange treatment.

The next step in the process of the present invention is the fractionation of the solution of the polyols obtained by hydrogenation into a xylitol-rich fraction and a polyol molasses. The hydrogenated solution prepared as described above contains a mixture of polyols; a typical composition of a hydrogenated birch wood hydrosalate as follows:

| Polyol | Percent, Dry Solids Basis |
| --- | --- |
| Xylitol | 77 |
| Arabinitol | 7 |
| Mannitol | 8 |
| Galactitol | 4 |

-continued

| Polyol | Percent, Dry Solids Basis |
|---|---|
| Sorbitol | 4 |

The mixture of polyols is separated by ion exchange chromatography and fractions are selected which provide a solution which is rich in xylitol. The purified solution thus obtained is readily processed to provide crystallized xylitol therefrom. Other polyols present in the solution, that is the arabinitol, mannitol, galactitol and sorbitol, may either be recovered from other selected fractions or collected into a polyol molasses.

While the hydrogenated polyol solution may be supplied directly to the fractionation column, it is technically sometimes advantageous to first crystallize a portion of xylitol from the impure solution, to separate the crystals, and to then fractionate the sugar alcohols remaining in the solution chromatographically. In addition, the solution remaining after the crystallizaton and separation of the crystals therefrom may be recirculated to a subsequent crystallization step in in order to improve the yield of crystals. This procedure is illustrated in FIG. 3.

EXAMPLE II

As an example of the application of a chromatographic fractionation step to the polyol solution, a column of ion exchange resin, specifically, a sulfonated polystyrene cation exchange resin, cross-coupled with a 3.5% di-vinyl benzene, in strontium form, is provided in a column one meter in depth and 9.4 centimeters in diameter. The column is prepared for use by submerging it in water. Means are provided to insure uniform introduction of the feed solution across the column. The feed solution has a solids concentration of 25% and a polyol analysis, by gas-liquid chromatographic analysis, as follows:

| Polyol | Percent, Dry Solids Basis |
|---|---|
| Xylitol | 75.5 |
| Arabinitol | 8.9 |
| Mannitol | 7.5 |
| Galactitol | 3.9 |
| Sorbitol | 4.3 |

The feed solution is fed to the column at a temperature of 50° C and at a feed rate of 27 ml per minute. The total amount of solution fed is 58.5 grams and the solids concentration thereof was 25%. Table I below shows the distribution of polyols in successive fractions collected during the chromatographic fractionation. Before collection of fractions commenced, 216 ml of solution, mostly comprised of the water originally in the column, was collected and discarded.

Table I

| Frac-tion | Grams of: | | | | |
|---|---|---|---|---|---|
| | Arabinitol | Mannitol | Galactitol | Xylitol | Sorbitol |
| 1 | 0.65 | 0.85 | — | — | — |
| 2 | 1.85 | 1.70 | — | — | — |
| 3 | 1.95 | 1.40 | 0.3 | — | — |
| 4 | 0.10 | 0.45 | 1.0 | 1.4 | — |
| 5 | — | — | 0.9 | 10.5 | — |
| 6 | — | — | 0.1 | 14.3 | 0.3 |
| 7 | — | — | — | 10.1 | 0.65 |
| 8 | — | — | — | 4.8 | 0.85 |
| 9 | — | — | — | 2.15 | 0.5 |
| 10 | — | — | — | 0.85 | 0.2 |

A xylitol-rich fraction is obtained by combining a part of fraction 5 with fractions 6 and 7. The solution thus obtained, 430 ml in amount, has the following analysis:

| Polyol | Grams |
|---|---|
| Arabinitol | 0.05 |
| Mannitol | — |
| Galactitol | 0.55 |
| Xylitol | 29.65 (=95%) |
| Sorbitol | 0.95 |

Crystalline xylitol is obtained from xylitol-rich solutions of the type described above by simple evaporation of the water contained therein. For example, 2,000 grams of a xylitol solution having a solids concentration of 80% and xylitol purity of 95% of the solids, when held at 60° C for 12 hours, provides 1,200 grams of crystalline xylitol having a purity of over 99.5%.

EXAMPLE III

A xylose-rich solution obtained as shown in FIG. 1 may be purified advantageously by chromatographic fractionation and subsequent crystallization. The purified pentose solutions contains several sugars in addition to xylose and the solution can be greatly enriched with respect to xylose by utilizing chromatographic fractionation techniques. In carrying out this example, a chromatographic column comprising a strongly acid cation exchanger in the form of a sulfonated polystyrene, cross-coupled with 3.5% of di-vinyl benzene, in strontium form, is contained in a column 1.0 meter high and 9.4 centimeters in diameter. The resin is submerged with water. A pentose solution containing 25% solids and having the following composition was used as the feed solution:

| Sugar | Percent, Dry Solids Basis |
|---|---|
| Xylose | 73 |
| Arabinose | 6.1 |
| Mannose | 9.0 |
| Galactose | 5.1 |
| Glucose | 6.8 |

The solution was uniformly fed across the top of the column at the rate of 27 ml per minute until a total of 60 grams of solids are fed to the column. The first 108 ml of material through the column comprising mostly the water originally in the column, are discarded. An analysis of the fractions obtained thereafter is given in Table II below.

Table II

| Frac-tion | Grams of: | | | | |
|---|---|---|---|---|---|
| | Glucose | Xylose | Mannose | Galactose | Arabinose |
| 1 | 0.2 | — | — | — | — |
| 2 | 0.35 | — | — | — | — |
| 3 | 0.75 | 0.2 | — | — | — |
| 4 | 1.1 | 0.9 | — | — | — |

Table II-continued

| Frac-tion | Grams of: | | | | |
|---|---|---|---|---|---|
| | Glucose | Xylose | Mannose | Galactose | Arabinose |
| 5 | 1.0 | 4.4 | 0.05 | — | — |
| 6 | 0.45 | 9.05 | 0.3 | 0.1 | — |
| 7 | 0.2 | 11.65 | 0.6 | 0.3 | — |
| 8 | 0.05 | 9.8 | 1.0 | 0.6 | — |
| 9 | — | 5.0 | 1.3 | 0.9 | — |
| 10 | — | 1.85 | 1.05 | 0.6 | 0.5 |
| 11 | — | 0.75 | 0.7 | 0.35 | 0.8 |
| 12 | — | 0.2 | 0.35 | 0.15 | 1.1 |
| 13 | — | — | 0.05 | 0.05 | 0.8 |
| 14 | — | — | — | — | 0.4 |
| 15 | — | — | — | — | 0.1 |

By combining fractions 6, 7 and 8, applicants obtained a solution having a xylose purity of 89%.

This xylose-rich fraction can be used in the production of a pure crystalline xylose. Alternatively the xylose-rich solution obtained by combining fractions 6, 7 and 8 may be hydrogenated as shown in FIG. 1 to obtain a relatively pure xylitol solution. It is additionally possible to crystallize the xylose from the impure solution, such as the feed solution used above in this example, and to thereafter fractionate the sugars which remain in the syrup by chromatographic procedures using ion exchanger resins. The xylose-rich fraction is recirculated to the crystallization step. It is also possible to obtain other pentoses and hexoses from corresponding fractions or the balance of the fractions may be combined into a pentose molasses.

EXAMPLE IV

Figure 4:
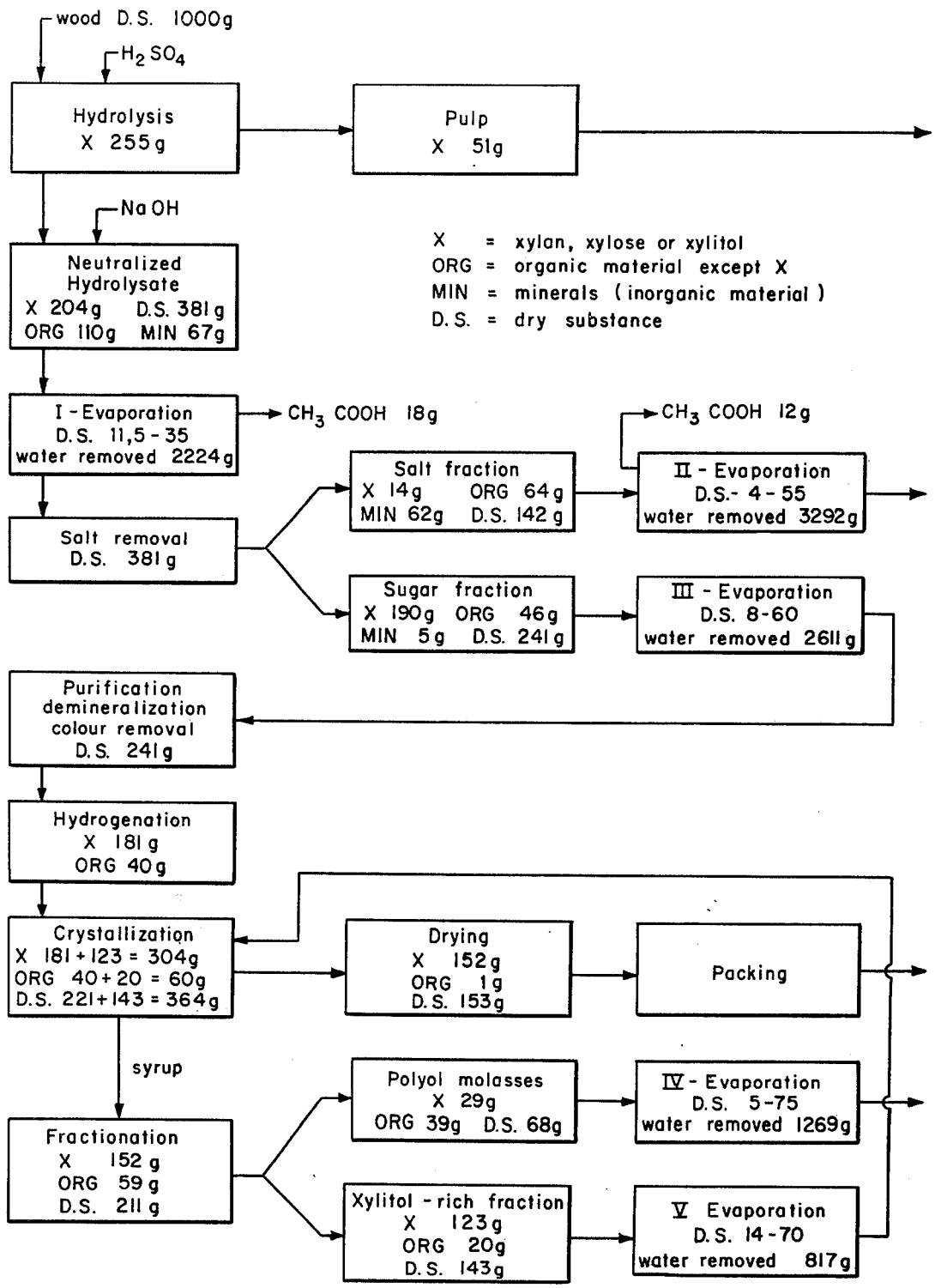
FIG. 4 is a flow diagram with material balance scheme for a process of preparing xylitol from wood chips.

Birch wood in the form of chips is used to prepare xylitol in accordance with the process of the present invention. A material balance scheme for this example is given in FIG. 4 of the drawings.

In accordance with the process of this example, sufficient birch wood chips to provide 1,000 grams of dry substance are hydrolyzed with sulfuric acid to provide a mixture of hydrolysate and pulp which contains totally 225 grams of xylose. The pulp, containing 51 grams of xylan is removed from the hydrolysate and either discarded or used for some other purpose. The balance of the hydrolysate containing 204 grams of xylose is neutralized with sodium hydroxide to provide a hydrolysate containing 204 grams of xylose, 110 grams of organic material exclusive of xylose and 67 grams of inorganic material. The hydrolysate is then heated to drive off unwanted acidic acid and water, and then subjected to a step of salt removal by ion exclusion and purification by passing the solution through successive beds of strong cation exchanger and weak anion exchanger. As shown in the drawing, 14 grams of xylose together with a major portion of the inorganic material and some of the organic material are removed and discarded in the salt fraction. The sugar fraction, containing most of the xylose together with a portion of the organic impurities and a small amount of inorganic impurities are again subjected to an evaporation step to remove additional quantities of water.

The concentrated sugar solution thus obtained as passed through a color removal step and activated carbon bed. The thus purified solution, containing 181 grams of xylose together with 40 grams of organic material, is hydrogenated. After hydrogenation, the solution is heated to evaporate a portion of the water, and from the concentrated solution xylitol is crystallized. The mother liquor remaining after removal of the crystalline xylitol is passed through a chromatographic ion exchange column, certain fractions being selected to provide a xylitol-rich fraction and the balance going into the polyol and molasses fraction. The xylitorl-rich fraction is concentrated by removal of water and returned to earlier crystallization stage where the xylitol is recovered. As can be seen from FIG. 4 of the drawings, the yield in terms of xylitol obtained from a given amount of raw material is high; approximately 60% of the original xylan content of the raw material is recovered as xylitol.

EXAMPLE V

A xylose-rich solution obtained by hydrolysis of birch wood, followed by salt removal and color removal procedures as described above, was further purified by chromatographic fractionation on an ion exchange resin column in accordance with the procedure described below. The composition of the solids content of the xylose-rich solution as determined by gas chromatographic analysis, was:

| Sugar | Percent |
|---|---|
| Arabinose | 6 |
| Xylose | 78 |
| Mannose | 7.5 |
| Galactose | 5 |
| Glucose | 4.5 |

The resin employed was a strongly acid cation exchanger, sulfonated polystyrene cross-coupled with 3.5% of di-vinyl benzene, the resin being in calcium form. The resin had a mean particle size of 0.32 mm. The separation was conducted at a temperature of 49° C. The column was 350 cm in height and had a diameter of 22.5 cm. The column was submerged in water. The xylose-rich solution was fed uniformly across the column at a rate of 17 liters per hour. The total amount fed to the column was four kilograms of solids, as a solution having a solids content of 26%.

The first effluent from the column, in the amount of 88 liters and mostly comprising water, was discarded. Thereafter, successive fractions were collected and analyzed, with the following results:

| Frac-tion | Dry Substance, Grams | | | | |
|---|---|---|---|---|---|
| | Glucose | Xylose | Mannose | Galactose | Arabinose |
| 1 | 8 | 41 | — | — | — |
| 2 | 91 | 165 | — | — | — |
| 3 | 75 | 497 | — | — | — |
| 4 | 8 | 704 | 25 | — | — |
| 5 | — | 720 | 91 | 25 | — |
| 6 | — | 580 | 124 | 83 | — |
| 7 | — | 289 | 58 | 41 | 8 |
| 8 | — | 83 | 7 | — | 66 |
| 9 | — | 8 | — | — | 99 |
| 10 | — | — | — | — | 66 |

Fractions 3 through 6 were combined to provide 35 liters of a xylose-rich solution which had the following analysis:

| Sugar | Grams |
|---|---|
| Arabinose | — |
| Xylose | 2483 (=85%) |
| Mannose | 240 |
| Galactose | 108 |

-continued

| Sugar | Grams |
| --- | --- |
| Glucose | 83 |

EXAMPLE VI

A xylose-rich solution obtained by hydrolysis of birch wood followed by salt removal and color removal procedures as described above was further purified by chromatographic fractionation on an ion exchange resin column as described below. The composition of the solids content of the xylose-rich solution, as determined by gas chromatographic analysis, was:

| Sugar | Percent |
| --- | --- |
| Arabinose | 6.5 |
| Xylose | 77 |
| Mannose | 8 |
| Galactose | 4 |
| Glucose | 4.5 |

The resin employed was a strongly acid cation exchanger, sulfonated polystyrene cross-coupled with 3.5% of di-vinyl benzene, the resin being in strontium form. The resin had a mean particle size of 0.32 mm. The separation was conducted at a temperature of 51° C. The column was 350 cm in height and had a diameter of 22.5 cm. The column was submerged in water. The xylose-rich solution was fed uniformly across the column at the rate of 15 liters per hour and the total amount of solids supplied to the column was four kilograms, in the form of a solution having a solids content of 28%.

The first effluent from the column, in the amount of 88 liters and comprising mostly water, was discarded. Thereafter, successive fractions were collected and analyzed, with the following results:

| Fraction | Dry substance, Grams | | | | |
| --- | --- | --- | --- | --- | --- |
|  | Glucose | Xylose | Mannose | Galactose | Arabinose |
| 1 | 8 | 41 | — | — | — |
| 2 | 83 | 157 | — | — | — |
| 3 | 75 | 447 | — | — | — |
| 4 | 7 | 662 | — | — | — |
| 5 | — | 696 | 33 | 8 | — |
| 6 | — | 580 | 91 | 40 | — |
| 7 | — | 331 | 108 | 75 | 25 |
| 8 | — | 124 | 66 | 33 | 91 |
| 9 | — | 41 | 17 | 7 | 99 |
| 10 | — | 10 | — | — | 41 |

Fractions 3 through 6 were combined to provide 35 liters of a xylose-rich solution which had the following analysis:

| Sugar | Grams |
| --- | --- |
| Arabinose | — |
| Xylose | 2385 (=90%) |
| Mannose | 124 |
| Galactose | 48 |
| Glucose | 82 |

EXAMPLE VII

This example illustrates the separation of sugar alcohols by chromatographic fractionation on an ion exchange resin column. The resin used was a strongly acid cation exchanger, sulfonated polystryene cross-coupled with 3.5% di-vinyl benzene, the resin being in calcium form. The resin had a mean particle size of 0.32 mm. The separation was conducted at 49° C. The column was 350 cm in height and had a diameter of 22.5 cm. The column of resin was submerged in water. The polyol solution was fed uniformly across the column at a feed rate of 17 liters per hour, and the total amount of solids fed to the column was four kilograms in the form of a solution having a solids concentration of 26%. The composition of the polyol solution, as determined by gas chromatographic analysis, was:

| Polyol | Percent |
| --- | --- |
| Arabinitol | 8 |
| Xylitol | 63 |
| Mannitol | 7 |
| Galactitol | 5 |
| Sorbitol | 4 |
| Unknown | 13 |

Figure 5:
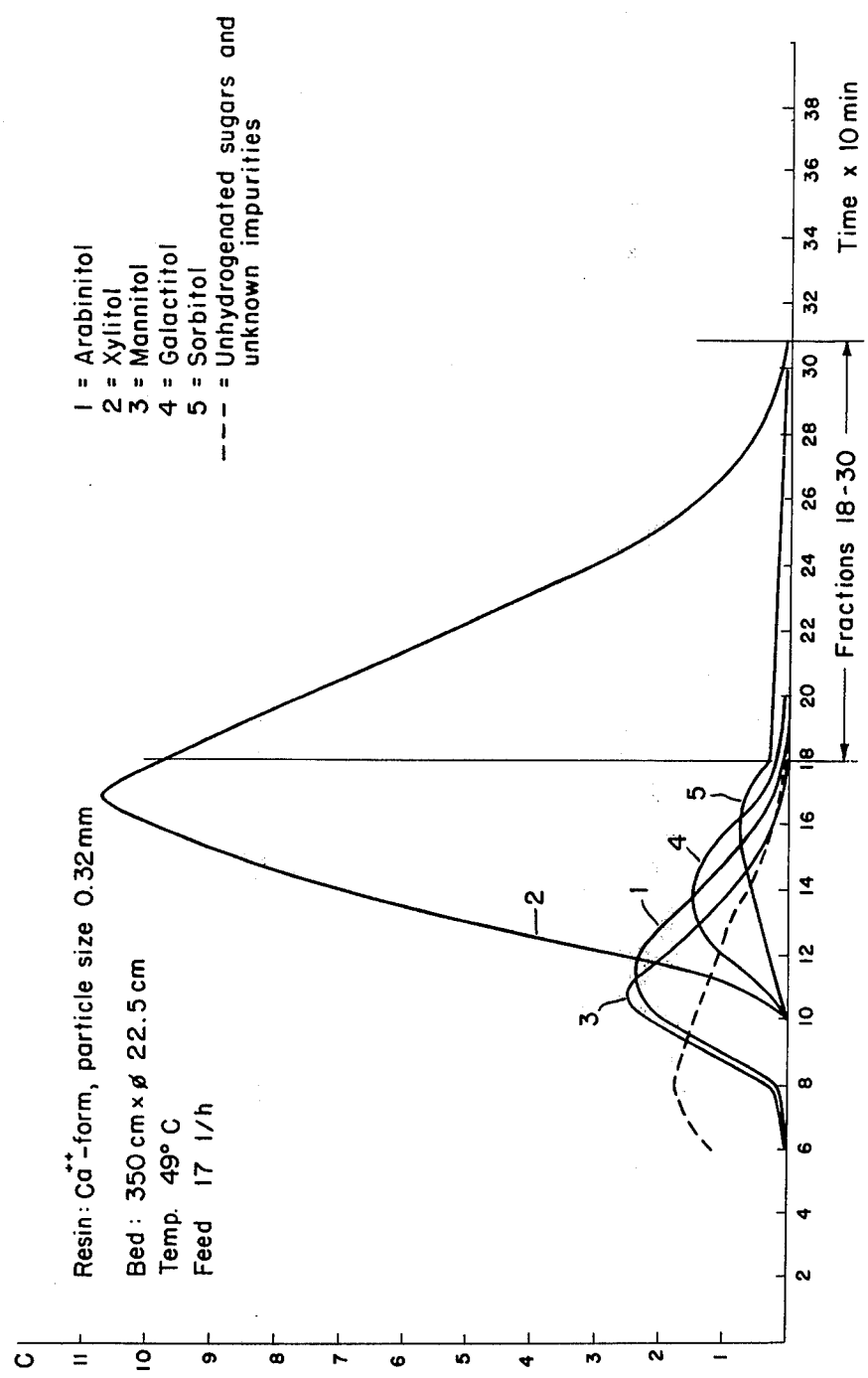
FIG. 5 is a graph showing distribution of various polyols in successive fractions taken during chromatographic separation of a solution of polyols in accordance with Example VII, supra.

The degree of separation of the sugar alcohols obtained in accordance with this example is shown in FIG. 5 of the drawings. A number of fractions were taken. A useful xylitol-rich fraction was recovered by combining fractions 18 through 30. In this manner, a solution in the amount of 34 liters was obtained having the following analysis:

| Polyol | Grams |
| --- | --- |
| Arabinitol | — |
| Xylitol | 1510 (=96%) |
| Mannitol | — |
| Galactitol | 13 |
| Sorbitol | 130 |

EXAMPLE VIII

This example illustrates the separation of sugar alcohols by chromatographic fractionation on an ion exchange resin column. The resin used was a strongly acid cation exchanger, sulfonated polystyrene cross-coupled with 3.5% di-vinyl benzene, the resin being in strontium form. The resin had a mean particle size of 0.32 mm. The separation was conducted at 51° C. The column was 350 cm in height and had a diameter of 22.5 cm. The column of resin was submerged in water. The polyol solution was fed uniformly across the column at a feed rate of 15 liters per hour and the total amount of solids fed to the column was four kilograms in the form of a solution having a solids concentration of 28%. The composition of the polyol feed solution, as determined by gas chromatographic analysis, was:

| Polyol | Percent |
| --- | --- |
| Arabinitol | 10 |
| Xylitol | 66 |
| Mannitol | 8 |
| Galactitol | 5 |
| Sorbitol | 5 |

-continued

| Polyol | Percent |
|---|---|
| Unknown | 6 |

Figure 6:
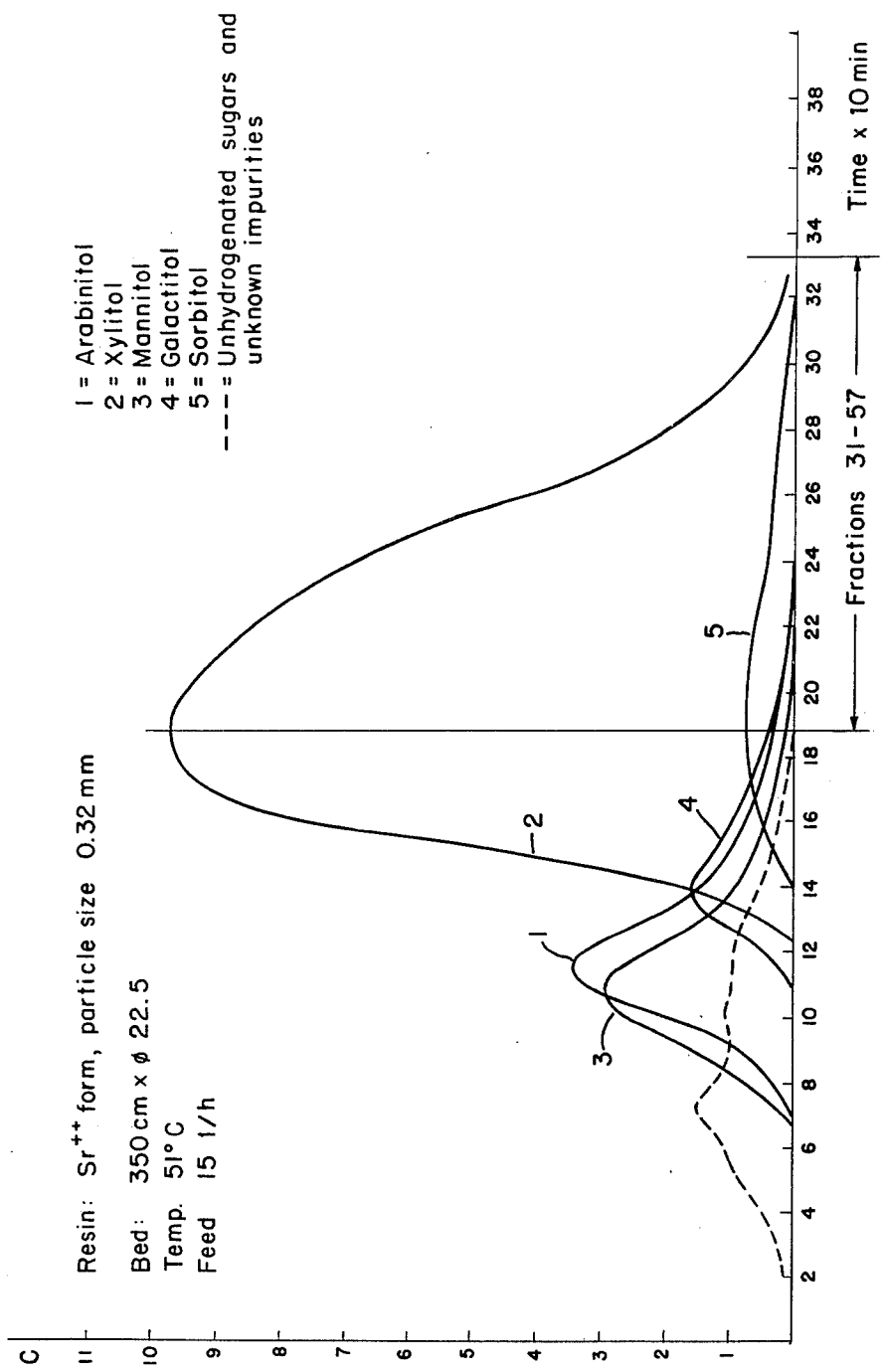
FIG. 6 is a graph showing distribution of various polyols in successive fractions taken during chromatographic separation of a solution of polyols in accordance with Example VIII, supra.

The degree of separation of the sugar alcohols obtained in accordance with this example is shown in FIG. 6 of the drawings. A number of fractions were taken. A useful xylitol-rich fraction was recovered by combining fractions 31 through 57. In this manner, a solution in the amount of 40 liters was obtained having the following analysis:

| Polyol | Grams |
|---|---|
| Arabinitol | 27 |
| Xylitol | 1792 (=90%) |
| Mannitol | 12 |
| Galactitol | 28 |
| Sorbitol | 140 |

EXAMPLE IX

This example illustrates the separation of unhydrogenated sugars and polyols from a hydrogenated pentose solution by chromatographic fractionation on an ion-exchange column 1 meter high and 10 cm in diameter. The resin used was a strongly acid cation exchanger, sulfonated polystyrene cross-coupled with 3.5% di-vinyl benzene, the resin being in calcium form. The resin had a mean particle size of 0.25 mm. The separation was conducted at 50° C and the feed rate was 0.30 l/hour. The feed stock comprised a hydrogenated mixture with 57 g. of solids as a 28% aqueous solution. The composition of the solids was as follows:

| Polyol | Percent |
|---|---|
| Xylitol | 77.0 |
| Arabinitol | 3.5 |
| Mannitol | 7.0 |
| Galactitol | 3.5 |
| Sorbitol | 3.5 |
| Unknown impurities | 3.0 |
| Xylose | 2.0 |

A number of fractions were collected and analyzed by gas-chromatography, with the following results:

| Fraction | Xylose | Unknown | Mannitol | Arabinitol | Galactitol | Xylitol | Sorbitol |
|---|---|---|---|---|---|---|---|
| 1 | 0.55 | — | — | — | — | — | — |
| 2 | 0.65 | 0.2 | — | — | — | — | — |
| 3 | — | 0.75 | — | — | — | — | — |
| 4 | — | 0.65 | 0.4 | — | — | — | — |
| 5 | — | 0.15 | 1.9 | 0.3 | — | 0.05 | — |
| 6 | — | — | 1.65 | 1.2 | 0.05 | 1.8 | — |
| 7 | — | — | 0.15 | 0.6 | 0.6 | 4.45 | — |
| 8 | — | — | — | — | 1.1 | 8.15 | 0.1 |
| 9 | — | — | — | — | 0.3 | 9.0 | 0.6 |
| 10 | — | — | — | — | — | 8.1 | 0.5 |
| 11 | — | — | — | — | — | 6.5 | 0.4 |
| 12 | — | — | — | — | — | 4.65 | 0.3 |
| 13 | — | — | — | — | — | 1.55 | 0.15 |

By combining fractions 6–13, a polyol solution completely free from unhydrogenated sugars and unidentified impurities was obtained.

EXAMPLE X

This example illustrates the separation of hexitol from pentitols using a synthetic mixture of sorbitol and xylitol, and using sulfonated polystyrene cation exchange resins cross-coupled with 3.5% di-vinyl benzene. A series of resins were evaluated, including each of the following catio forms: $H^+$, $Li^+$, $Ni^{++}$, $Mg^{++}$, $Fe^{+++}$, $NH_4^+$, $Al^{+++}$, $Cu^{++}$. Of these cations, $Fe^{+++}$ and $Al^{+++}$ give the best results. The results of the experiments are shown in the following table:

| | Fractionation of Xylitol and Sorbitol | | | | |
|---|---|---|---|---|---|
| Experiment No. | $K_D$ Sorbitol | $K_D$ Xylitol | HETP (cm) Xylitol | $R_s$ | Cation |
| 1 | 0.54 | 0.79 | 0.10 | 0.30 | $H^+$ |
| 2 | 0.52 | 0.53 | 0.23 | 0.07 | $Li^+$ |
| 3 | 0.49 | 0.54 | 0.40 | 0.27 | $Mg^{++}$ |
| 4 | 0.42 | 0.45 | 0.13 | 0.24 | $Ni^{++}$ |
| 5 | 0.42 | 0.48 | 0.11 | 0.44 | $Fe^{+++}$ |
| 6 | 0.54 | 0.59 | 0.11 | 0.33 | $NH_4^+$ |
| 7 | 0.41 | 0.48 | 0.10 | 0.48 | $Al^{+++}$ |
| 8 | 0.45 | 0.50 | 0.12 | 0.41 | $Cu^{++}$ |

Calculated: $K_D$ = distribution coefficient
HETP = value for xylitol
$R_s$ = resolution The distribution coefficients, HETP values and the resolution values for the separations were calculated. These values are the parameters normally used for the evaluation of column separations, and are calculated according to the following formulae:

$$K_D = \frac{V_e - V_o}{V_t}$$

$$HETP = \frac{h}{N} = \frac{h}{16 \times \left(\frac{V_e^2}{M}\right)}$$

$$R_s = \frac{2(V_{e2} - V_{e1})}{M_2 + M_1}$$

$K_D$ = distribution coefficient
HETP = height of theoretical plate
$R_s$ = resolution
$V_e$ = elution volume for the peak
$V_o$ = void volume of the column
$V_t$ = total volume of the column
h = height of the column
N = number of theoretical plates
M = band width of eluted peak, measured on volume (or time) axis in volume (or time) units.

From the examination of the table above, it is evident that sorbitol is eluted before xylitol and that $Fe^{+++}$ and $Al^{+++}$ give the best separation.

The conditions used in this example were as follows:

| Separation of Sorbitol and Xylitol | |
|---|---|
| Column | height, 84 cm; diameter, 4.4 cm |
| Temperature | 50° C |
| Feed Rate | 3.2 ml/min |
| Resin | (polystyrene sulfonate, cross-linked with 3–4% di-vinyl benzene) mean bead size 0.18 mm, $Al^{+++}$-form |
| Feed | a synthetic mixture of sorbitol and xylitol (1:1). Total amount 25 g dry substance, concentration 35% (weight) |

Figure 7:
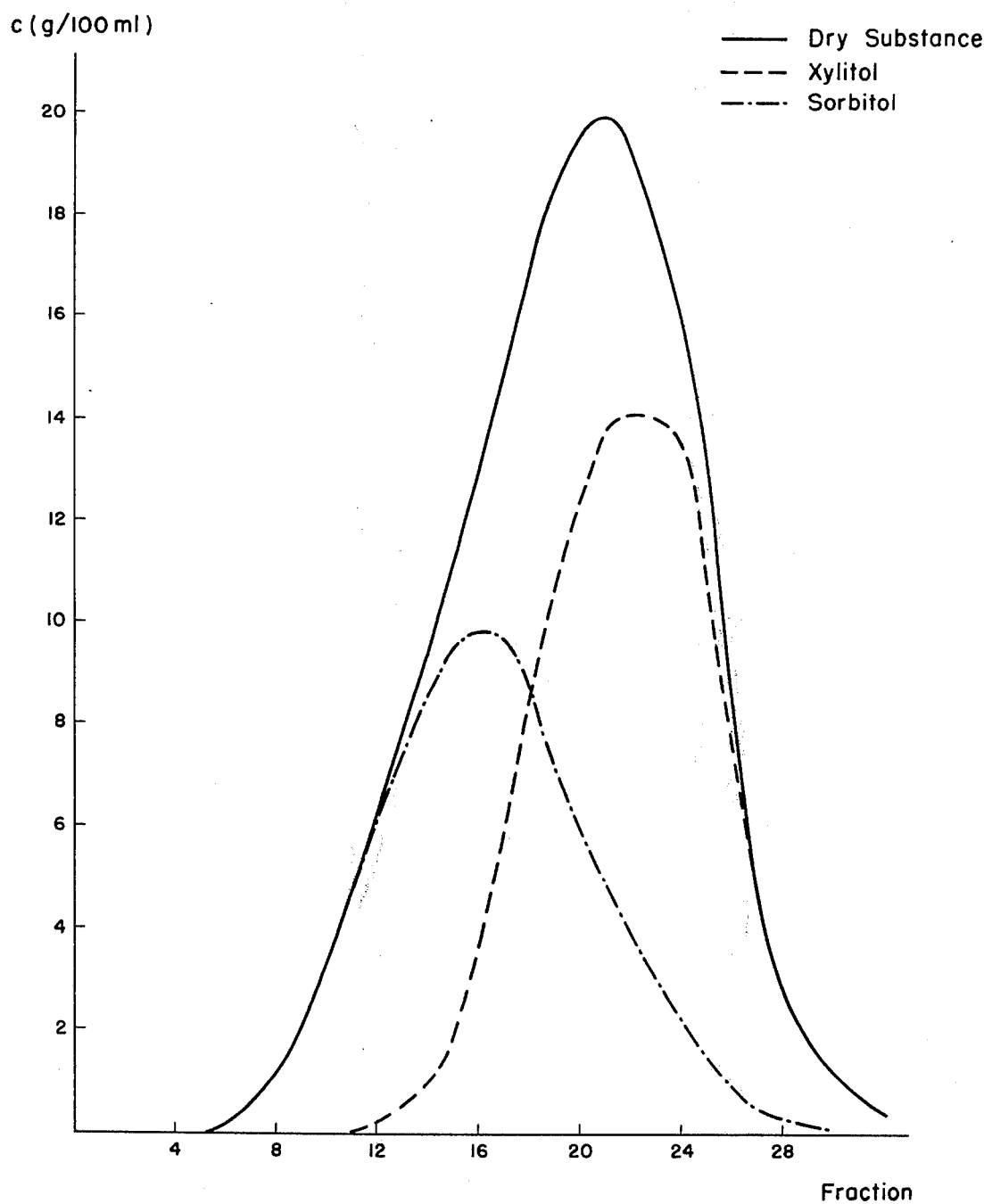
FIG. 7 is a graph showing distribution or sorbitol and xylitol in successive fractions taken during chromatographic separation of a solution containing a mixture of the two polyols on an $Al^{+++}$ form of the resin in accordance with Example X.

The results obtained in accordance with this example are shown in FIG. 7 in graph form.

EXAMPLE XI

Figure 8:
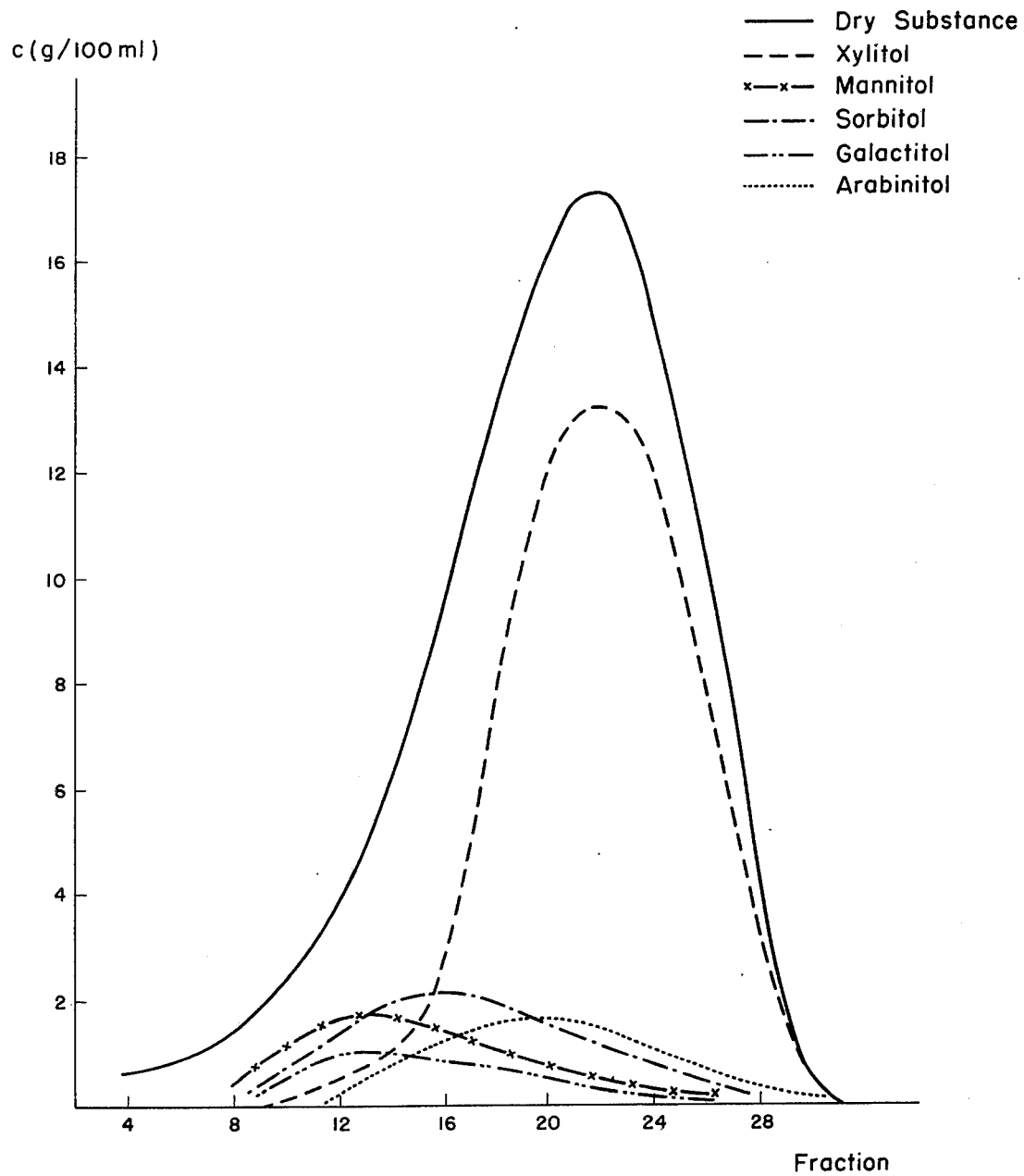
FIG. 8 is a graph showing distribution of five polyols in successive fractions obtained after chromatographic separation of a mixture thereof in accordance with the process described in Example XI.

This example shows the separation of each of five polyols from hydrogenated wood hydrolysates on the cation exchange resin described in Example X, using the $Fe^{+++}$ form. The results are shown graphically in FIG. 8. The conditions for this example were as follows:

| Separation of Polyols | |
|---|---|
| Column | height, 84 cm; diameter, 4.4 cm |
| Temperature | 52° C |
| Feed Rate | 3.2 ml/min |
| Resin | Polystyrene sulfonate with 3–4% DVB, mean bead size 0.18 mm, $Fe^{+++}$-form |
| Feed | Polyol solution, total amount 25 g dry substance, concentration 35%. |

The composition of the feed solution was as follows: 23.5 g total dry substance; concentration: 35 g/100 ml

| | Percent |
|---|---|
| Mannitol | 8.9 |
| Arabinitol | 9.1 |
| Galactitol | 5.1 |
| Xylitol | 64.0 |
| Sorbitol | 12.9 |

EXAMPLE XII

This example describes the separation of five polyols present in hydrogenated wood hydrolysates on the cation exchange resin described in Example X, using the $Al^{+++}$ form. The conditions of the separation were as follows:

| Separation of polyols | |
|---|---|
| Column | height, 82 cm; diameter, 4.4 cm |
| Temperature | 51° C |
| Feed Rate | 3.2 ml/min |
| Resin | As in Example X, $Al^{+++}$-form |
| Feed | Polyol solution, total amount 23.5 g dry substance, concentration 34.9%, composition given in Example XI above. |

The results obtained are summarized in the following tables:

| | Separation of Polyols on Resin in $Al^{+++}$-Form | | | | | | | | |
|---|---|---|---|---|---|---|---|---|---|
| Fraction (20 ml) | Mannitol g | | Arabinitol g | | Galactitol g | | Xylitol g | | Sorbitol g |
| | a) | b) | | | | | | | |
| 1 | 0.09 | 0.09 | — | — | — | — | — | — | 0.02 | 0.02 |
| 2 | 0.18 | 0.27 | — | 0.05 | 0.05 | — | — | 0.18 | 0.20 |
| 3 | 0.27 | 0.54 | 0.07 | 0.07 | 0.13 | 0.18 | 0.02 | 0.02 | 0.34 | 0.54 |
| 4 | 0.39 | 0.93 | 0.18 | 0.25 | 0.23 | 0.41 | 0.23 | 0.25 | 0.56 | 1.10 |
| 5 | 0.43 | 1.36 | 0.27 | 0.52 | 0.27 | 0.68 | 0.52 | 0.77 | 0.66 | 1.76 |
| 6 | 0.34 | 1.70 | 0.39 | 0.91 | 0.23 | 0.91 | 1.92 | 2.69 | 0.56 | 2.32 |
| 7 | 0.23 | 1.93 | 0.43 | 1.34 | 0.16 | 1.07 | 3.05 | 5.74 | 0.34 | 2.66 |
| 8 | 0.11 | 2.04 | 0.39 | 1.73 | 0.09 | 1.16 | 3.29 | 9.03 | 0.21 | 2.87 |
| 9 | 0.05 | 2.09 | 0.29 | 2.02 | 0.05 | 1.21 | 3.05 | 12.08 | 0.11 | 2.98 |
| 10 | — | — | 0.13 | 2.15 | — | — | 2.03 | 14.11 | 0.05 | 3.03 |
| 11 | — | — | — | — | — | — | 0.79 | 14.90 | — | — |
| 12 | — | — | — | — | — | — | 0.13 | 15.03 | — | — |
| Total | | 2.09 | | 2.15 | | 1.21 | | 15.03 | | 3.03 |
| | | 8.9 % | | 9.1 % | | 5.1 % | | 64.0 % | | 12.9 % |

Distribution of polyols when the fractions are combined a) 1–6 / 7–12 or b) 1–7 / 8–12. Polyols, as % of total amount

| Polyol | Combination | | Combination | |
|---|---|---|---|---|
| | 1 – 6 | 7 – 12 | 1 – 7 | 8 – 12 |
| Mannitol | 82% | 18% | 92% | 8% |
| Arabinitol | 42 | 58 | 62 | 38 |
| Galactitol | 76 | 24 | 89 | 11 |
| Xylitol | 18 | 82 | 38 | 62 |
| Sorbitol | 77 | 23 | 88 | 12 |

Figure 9:
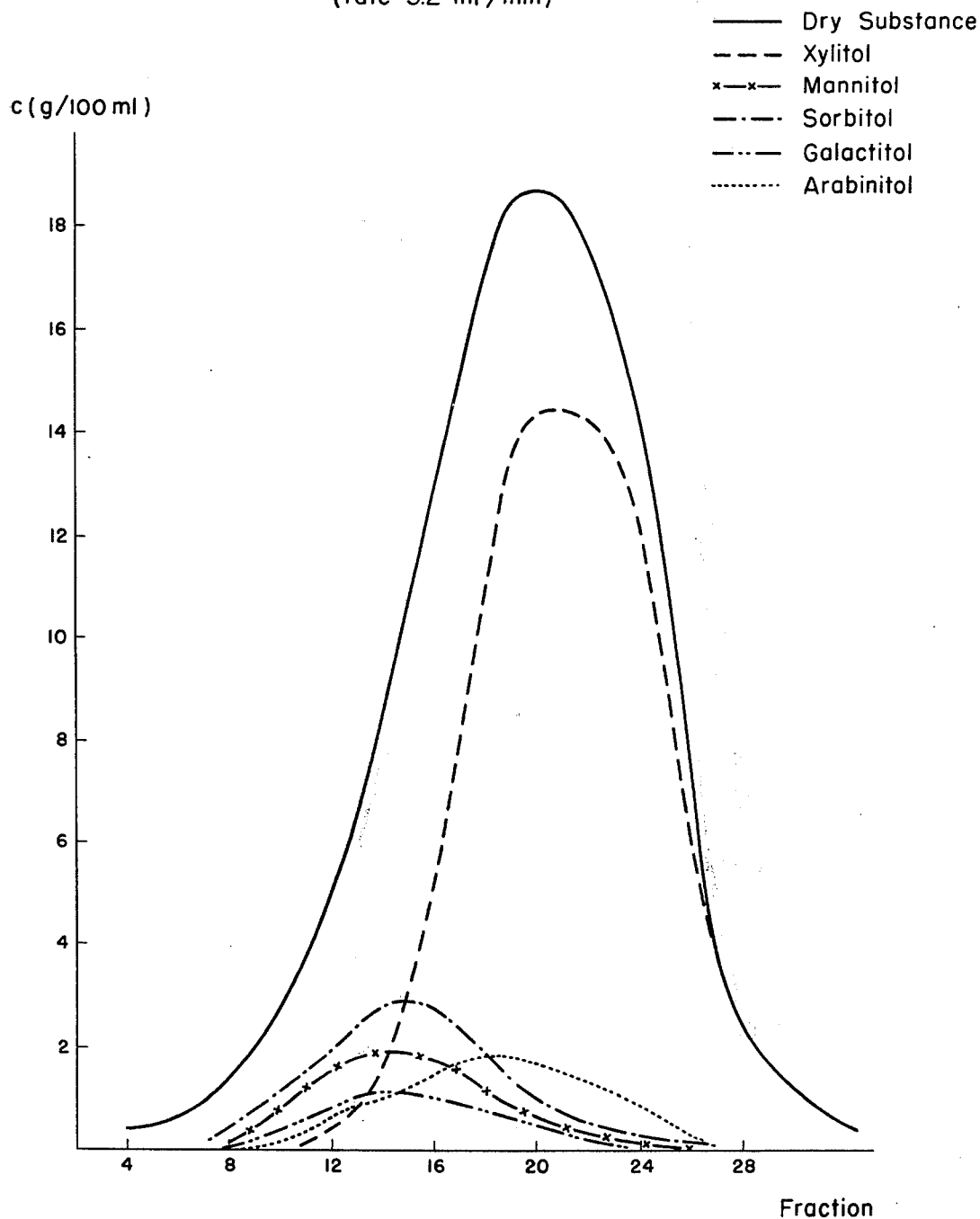
FIG. 9 is a graph showing distribution of various polyols in successive fractions taken during the chromatographic separation of a solution thereof in accordance with Example XII.

In addition, FIG. 9 of the Drawings is a graph illustrating the results obtained in accordance with the process of this example.

EXAMPLE XIII

This example illustrates a process similar to that of Example XII above and differs therefrom only in the feed rate used. The column dimensions and resins used were the same as those in Example XII. The temperature used was 50° C and the feed rate was 2.2 ml per minute. The feed solution was a polyol solution, 25 grams in total amount containing 35% of dry substance.

Figure 10:
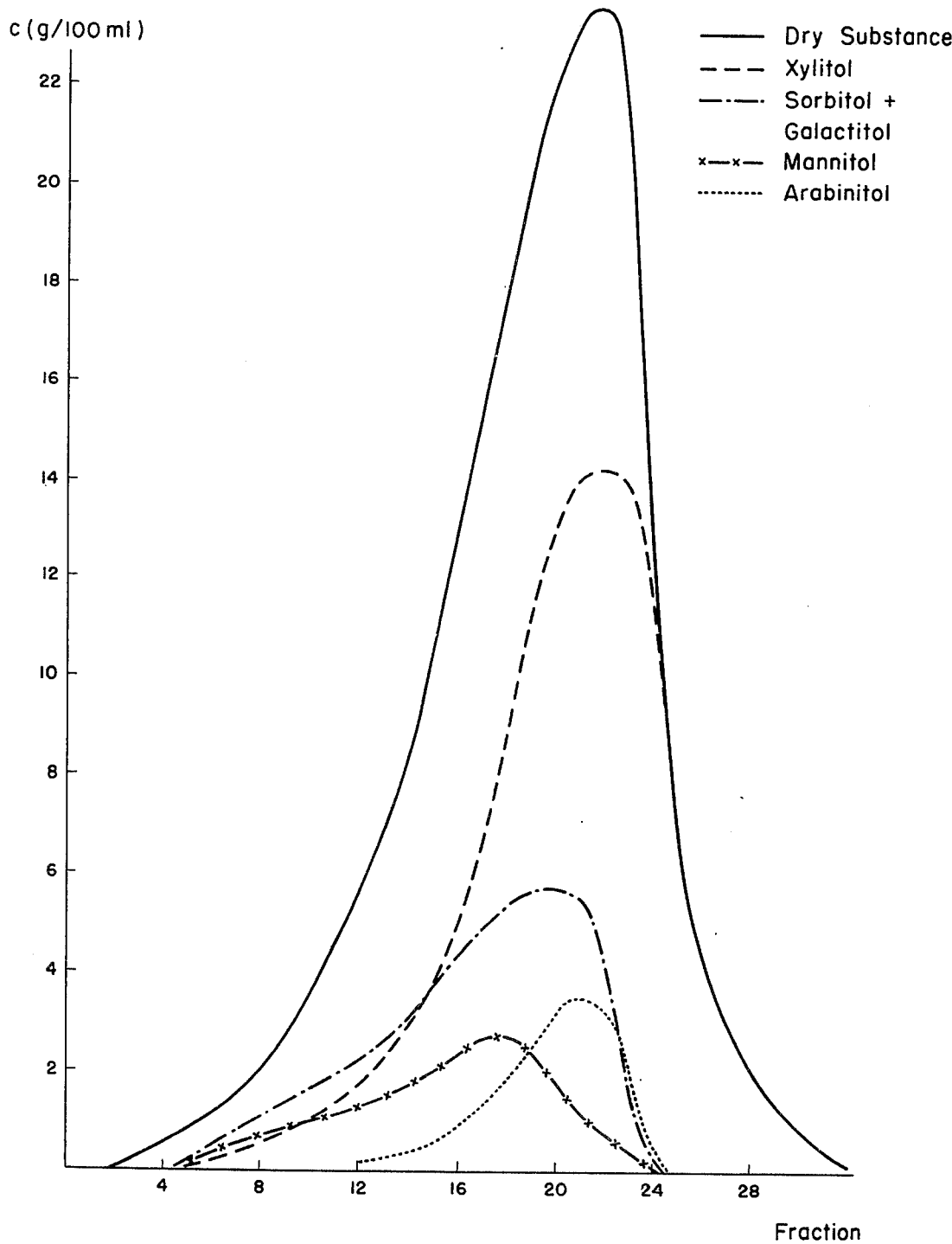
FIG. 10 is a graph showing distribution of various polyols in successive fractions taken during chromatographic separation of a solution of polyols in accordance with Example XIII.

The results obtained in this example are shown in FIG. 10.

EXAMPLE XIV

The following example describes a double fractionation procedure which is useful in the production of xylitol in accordance with the process of the present invention.

In the first stage of the procedure, a hydrogenated wood hydrolysate is fractionated on a resin in alkaline earth metal form and three fractions are collected from the effluent, namely, a xylitol-rich fraction, a polyol fraction and a waste fraction. Xylitol is crystallized from the xylitol-rich fraction and the xylitol crystals are separated from the mother syrup by centrifuging. The mother syrup which remains from the centrifugation is combined with the polyol fraction obtained from the first fractionation above and the resulting combined polyol solution is then subjected to a second fractionation on a resin in $Al^{+++}$ or $Fe^{+++}$ form.

Three fractions are again collected from the effluent of the second fractionation namely, a xylitol-rich fraction, a polyol fraction and a waste fraction. The xylitol-rich fraction from this second fractionation is combined with the xylitol-rich fraction from the first fractionation and from the combined solution, xylitol is recovered by concentration and crystallization. The polyol fraction from the second fractionation is added to the next batch of feed solution to the first fractionation and the combined solution is fractionated on the column of alkaline earth metal form resin as described for the first fractionation.

The process was carried out in detail as follows:

| Production of Xylitol | | | |
|---|---|---|---|
| Feed solution | Arabinitol | 5.2 % | of dry substance |
| | Xylitol | 77.0 % | |
| | Mannitol | 8.7 % | |
| | Galactitol | 4.8 % | |
| | Sorbitol | 4.3 % | |

| | Fractionations | |
|---|---|---|
| | I | II |
| Resin | Polystyrene sulfonate with 3–4% DVB mean diameter 0.39 mm $Sr^{++}$-form | Polystyrene sulfonate with 3–4% DVB mean diameter 0.24 mm $Fe^{+++}$-form |
| Column | 350 cm, diameter 22.5 cm | 325 cm, diameter 22.5 cm |
| Temperature | 51° C | 47° C |
| Feed Rate | 27 l/h | 11 l/h |
| Feed | 3.0 kg concentration 22.8% composition above | 2.0 kg concentration 25.2% composition above |

Figure 11:
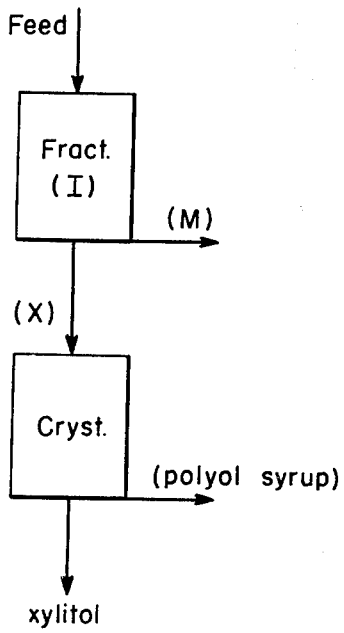
FIG. 11 is a flow diagram describing the single fractionation procedure described in Example XIV.

Single fractionation —Reference is made to the scheme in FIG. 11. Resin used was in $Sr^{++}$-form. A graph showing the results of this fractionation, in terms of the polyol distribution in successive fractions, is shown in FIG. 13. Referring to FIG. 11, the fractions are combined into a xylitol-rich fraction (X) and a mixed polyol fraction (M). From the xylitol fraction, xylitol is recovered by concentration and crystallization. The mother syrup from the crystallization may be partly recirculated to the process.

Figure 12:
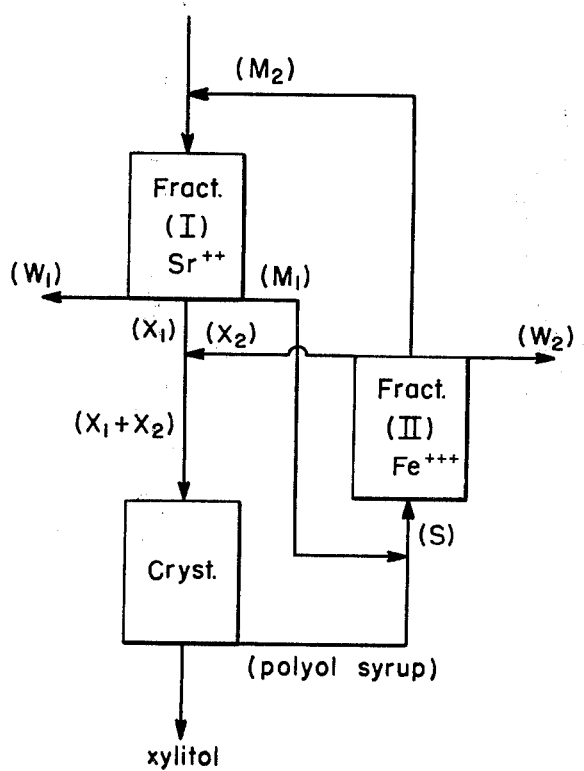
FIG. 12 is a flow diagram describing a double fractionation scheme described in Example XI.

Double fractionation —Referring to FIG. 12, the polyols are first fractionated as in the method with a single fractionation which is described above (resin in $Sr^{++}$-form). From the first fractionation, 3 fractions are recovered: a xylitol-rich fraction ($X_1$), a polyol fraction ($M_1$) and a waste fraction ($W_1$). From the waste fraction, xylitol cannot be recovered, but it still contains valuable carbohydrates. From the $X_1$, fraction, xylitol is recovered by concentration and crystallization. The polyol-syrup which is separated from the crystals is combined with the polyol fraction ($M_1$) from the first fractionation to provide a polyol solution (S) which contains large amounts of xylitol. This solution (S) is fractionated on a resin in $Fe^{+++}$-form and again 3 fractions are collected: a xylitol-rich fraction ($X_2$), a polyol fraction ($M_2$) and a waste fraction ($W_2$). The second xylitol fraction ($X_2$) is combined with the first xylitol fraction ($X_1$) and from the combined solution xylitol is recovered by concentration and crystallization. The second polyol fraction ($M_2$) is combined with the next batch of feed solution.

A graph showing the result of the double fractionation (fractionation II) is shown in FIG. 14.

Composition of the solutions and fractions:

| | Fractionation I | | |
|---|---|---|---|
| | Feed, 100% | $X_1$, 58% | $M_1$, 33% |
| Arabinitol | 5.2% of d.s. | 0.2% of d.s. | 6.7% of d.s. |
| Xylitol | 77.0% | 92.9% | 69.2% |
| Mannitol | 8.7% | 0.9% | 8.5% |
| Galactitol | 4.8% | 0.9% | 11.6% |
| Sorbitol | 4.3% | 5.2% | 4.0% |
| | | $W_1$, Waste fraction 9%. | |

| | Fractionation II | | |
|---|---|---|---|
| | S, 56% | $X_2$, 24% | $M_2$, 14% |
| Arabinitol | 4.1% | 3.7% | 5.7% |
| Xylitol | 74.4% | 87.8% | 70.9% |
| Mannitol | 6.1% | 2.0% | 7.1% |
| Galactitol | 7.7% | 2.4% | 9.0% |
| Sorbitol | 7.7% | 4.1% | 7.1% |
| | | $W_2$, Waste fraction 6% | |

The recovery of xylitol in the crystallization step was 65% of the xylitol present in the solution. The total recovery by double fractionation was 85–90% xylitol, which had a purity of over 99%. This is to be compared with a recovery of 50–55% of xylitol by the single fractionation procedure. At the same time, the double fractionation procedure avoids precipitation of significant quantities of galactitol with the xylitol crystals. Depending on the composition of the feed solution it might sometimes be advantageous to collect only two fractions: a xylitol-rich fraction and a waste fraction from both fractionation steps. Reference is made to FIG. 7 and to the tables of Example XII.

By way of explanation, where fractionations are carried out on resins in alkaline earth metal form and polyol fractions or portions thereof are recirculated to recover xylitol values therein, sorbitol tends to accumulate in the process. The reason for this can be seen from an examination of FIG. 13. The curves for xylitol and sorbitol show that no significant separation of these two polyols occurs on the $Sr^{+++}$ resin form. Thus, if xylitol were removed from the xylitol-rich fraction and the balance of the fraction was returned to the system, a build-up of sorbitol would occur. Use of the resin in $Al^{+++}$ or $Fe^{+++}$ resin form permits effective separation of sorbitol; it will be removed from a double fractionation system such as that shown in FIGS. 12 and 14 in the $W_2$ fraction in sufficient quantities to prevent its build-up within the system.

With regard to the galactitol, this substance has a very low solubility and it is thus important that it be separated from the xylitol before crystallization thereof because it tends to crystallize with the xylitol crystals. The double fractionation scheme shown in FIGS. 12 and 14 substantially reduces the galactitol impurity level in the xylitol crystals. It will be noted that a major part of the galactitol during fractionation I is found in the $M_1$ fraction. In fractionation II, however, the major part of the galactitol is separated into the $W_2$ fraction and thus removed from the system.

EXAMPLE XV

This example shows a good separation of xylitol from other polyols on a resin in $Al^{+++}$ form. The results of the test are shown in FIG. 15. The conditions of this example were as follows:

| Resin | Polystyrene-divinylbenzene in $Al^{+++}$-form |
| --- | --- |
|  | Mean particle size 0.21 mm |
| Temperature | 57° C |
| Feed rate | 8.2 l/h |

The composition of the feed solution was as follows: 1 kg of dry substance, concentration of 25.2%.
The polyol syrup had the following composition:

| Sugar | Percent of Dry Substance |
| --- | --- |
| Xylitol | 73 |
| Sorbitol | 12 |
| Mannitol | 11 |
| Galactitol | 2.5 |
| Arabinitol | 1.5 |

We claim:
1. A method for the production of xylitol on a commercial scale from a pentose-rich solution obtained by acid hydrolysis of a pentosan-containing raw material which comprises the steps of
   a. removing suspended solids from the solution by mechanical filtration;
   b. removing inorganic salts and the major portion of organic impurities and color from the solution by ion exclusion;
   c. removing the balance of color and other organic impurities by treating the solution with a material selected from the group consisting of an ion exchange resin and activated carbon;
   d. fractionating the solution thus obtained by ion exchange chromatographic techniques to provide a xylose solution of high purity;
   e. catalytically hydrogenating the xylose solution; and
   f. subjecting the xylitol solution thus produced to ion exchange chromatographic fractionation to recover a xylitol fraction of high purity.

2. The process of claim 1 wherein step (d) is accomplished by:
   a. providing a column of a salt of a polystyrene sulfonate cation exchange resin cross-coupled with divinyl benzene;
   b. submerging the column of resin in water;
   c. feeding the pentose-rich solution having a dry material content of 25 to 55% by weight in uniform supply to the resin surface in the column at a flow rate of 0.2 to 1.5 cubic meters per hour per square meter of the cross-section of the resin column; and
   d. recovering successively from the downstream side of the resin bed
      1. an inital fraction containing mostly water but also containing other pentoses and a low concentration of xylose,
      2. an intermediate fraction having a high concentration of xylose and small amounts of other pentoses, and
      3. a final fraction containing other pentoses and a minor amount of xylose.

3. The process of claim 1, wherein step (f) is accomplished by:
   a. providing a column of a salt of a polystyrene sulfonate cation exchange resin cross-coupled with divinyl benzene;
   b. submerging the column of resin in water;
   c. feeding the xylitol-rich solution having a dry material content of 25 to 55% by weight in uniform supply to the resin surface in the column at a flow rate of 0.2 to 1.5 cubic meters per hour per square meter of the cross-section of the resin column; and
   d. recovering successively from the downstream side of the resin bed
      1. an initial fraction containing mostly water but also containing other polyols and a low concentration of xylitol,
      2. an intermediate fraction containing a high concentration of xylitol, together with small amounts of other polyols; and
      3. a final fraction containing other polyols and a minor amount of xylitol.

4. The process of claim 3, wherein the salt of the resin is selected from the group consisting of alkaline earth metal salts, $Fe^{+++}$ salts and $Al^{+++}$ salts.

5. The process of claim 3, wherein the column of cation-exchanger, wherein used, is from 2.5 to 5 meters in depth.

6. The process of claim 3 wherein the resin used in step (a) is an alkaline earth metal salt.

7. A method for the production of a mixture of polyols on a commercial scale from a pentose-rich solution obtained by acid hydrolysis of a pentosan-containing raw material which comprises the steps of
a. removing suspended solids from the solution by mechanical filtration,
b. removing inorganic salts and the major portion of color and other organic impurities by ion exclusion;
c. removing the balance color and other organic impurities by treating the solution with a material selected from the group consisting of an ion exchanger resin and activated carbon;
d. fractionating the solution thus obtained by ion exchange chromatographic techniques to provide a pentose solution of high purity, and having a high concentration of pentoses.
e. catalytically hydrogenating the pentose solution to produce a mixture of polyols, and
f. subjecting the polyol mixture to ion exchange chromatographic fractionation to recover a polyol fraction of high purity, free of unhydrogenated sugars and other impurities.

8. The process of claim 7, wherein step (f) is accomplished by:
a. providing a column of a salt of a polystyrene sulfonate cation exchange resin cross-coupled with di-vinyl benzene;
b. submerging the column in water;
c. feeding the polyol solution in uniform supply to the resin surface in the column, and
d. recovering successively from the downstream side of the resin bed
1. a first fraction comprising unhydrogenated sugars and other impurities, and
2. a second fraction comprising substantially pure polyols.

9. The process of claim 8, wherein the second fraction comprising a mixture of polyols at (d) (2) is further separated by ion exchange chromatographic fractionation to recover the individual polyols in substantially pure form.

10. The process of claim 8, wherein the salt of the resin is selected from the group consisting of alkaline earth metal salts, $Fe^{+++}$ salts and $Al^{+++}$ salts.

11. The process of claim 8 wherein the salt of the resin is an alkaline earth metal salt.

12. The process of claim 8, wherein the salt of the resin is an $Fe^{+++}$ or $Al^{+++}$ salt, and wherein the second fraction comprising a mixture of polyols at (d) (2) is further separated by ion exchange chromatographic fractionation to recover the individual polyols in substantially pure form.

13. In a method for recovering xylitol on a commercial scale from an aqueous mixture of polyols which employs chromatographic techniques on a bed of polystyrene sulfonate cation exchange resin cross-coupled with di-vinyl benzene, the improvement comprising a two-stage fractionation procedure, one stage of the procedure comprising:
1. fractionation of the polyol mixture by passing it through a bed of said resin in an alkaline earth metal salt form to recover;
a. a waste fraction having a low concentration of xylitol, and
b. a xylitol-rich fraction;
2. crystallizing xylitol from the xylitol-rich fraction to obtain xylitol crystals and a polyol molasses;
3. subjecting the polyol molasses remaining after crystallization of the xylitol to a second stage fractionation procedure which comprises passing the molasses through a column of said resin in the $Al^{+++}$ or $Fe^{+++}$ form to recover;
a. a waste fraction containing a low level of xylitol, and
b. a xylitol-rich fraction;
4. recovering xylitol crystals from said xylitol-rich fraction, leaving a residual polyol molasses; and
5. returning the residual polyol molasses to the first stage of the separation procedure in admixture with new polyol mixture.

14. In a method for recovering xylitol on a commercial scale from an aqueous mixture of polyols which employs chromatographic techniques on a bed of polystyrene sulfonate cation exchange resin cross-coupled with di-vinyl benzene, the improvement comprising a two-stage fractionation procedure, one stage of the procedure comprising:
1. fractionation of the polyol mixture by passing it through a bed of said resin in an alkaline earth metal salt form to recover;
a. a waste fraction having a low concentration of xylitol,
b. an intermediate polyol molasses fraction, and
c. a xylitol-rich fraction;
2. crystallizing xylitol from the xylitol-rich fraction to obtain xylitol crystals and a polyol molasses;
3. combining the intermediate fraction in (1) (b) above with the polyol molasses obtained in (2) above to provide a polyol molasses feed for the next stage in the process;
4. subjecting the polyol molasses feed to a second stage fractionation procedure which comprises passing the molasses through a column of said resin in the $Al^{+++}$ or $Fe^{+++}$ form to recover;
a. a waste fraction containing a low level of xylitol,
b. an intermediate polyol molasses fraction, and
c. a xylitol-rich fraction;
5. recovering xylitol crystals from said xylitol-rich fraction, leaving a residual polyol molasses;
6. combining the residual polyol molasses from (5) above with the intermediate polyol molasses fraction from (4) (b);
7. returning the said combined polyol molasses fractions to the first stage of the separation procedure in admixture with new polyol mixture.

15. A method for the production of xylitol on a commercial scale from a pentose-rich solution obtained by acid hydrolysis of a pentosan-containing raw material which comprises the steps of
a. removing suspended solids from the solution by mechanical filtration;
b. removing inorganic salts and the major portion of organic impurities and color from the solution by ion exclusion;
c. removing the balance of color and other organic impurities by treating the solution with a material selected from the group consisting of an ion exchange resin and activated carbon;
d. fractionating the solution thus obtained by ion exchange chromatographic techniques to provide a xylose solution of high purity;
e. catalytically hydrogenating the xylose solution;
f. providing a column of $Fe^{+++}$ or $Al^{+++}$ salt of a polystyrene sulfonate cation exchange resin cross-coupled with di-vinyl benzene;
g. submerging the column of resin in water;

h. feeding the pentose-rich solution having a dry material content of 25 to 55% by weight in uniform supply to the resin surface in the column at a flow rate of 0.2 to 1.5 cubic meters per hour per square meter of the cross-section of the resin column; and i. recovering successively from the downstream side of the resin bed
   1. an initial fraction containing mostly water but also containing other polyols and a low concentration of xylitol,
   2. an intermediate fraction containing a high concentration of xylitol, together with small amounts of other polyols; and
   3. a final fraction containing other polyols and a minor amount of xylitol.

16. A method for the production of a mixture of polyols from a pentose-rich solution obtained by acid hydrolysis of a pentosan-containing raw material which comprises the steps of
   a. removing suspended solids from the solution by mechanical filtration,
   b. removing inorganic salts and the major portion of color and other organic impurities by ion exclusion;
   c. removing the balance of color and other organic impurities by treating the solution with a material selected from the group consisting of an ion exchanger resin and activated carbon;
   d. fractionating the solution thus obtained by ion exchange chromatographic techniques to provide a pentose solution of high purity, and having a high concentration of xylose,
   e. hydrogenating the pentose solution to produce a mixture of polyols,
   f. providing a column of an $Fe^{+++}$ or $Al^{+++}$ salt of a polystyrene sulfonate cation exchange resin cross-coupled with di-vinyl benzene;
   g. submerging the column in water;
   h. feeding the polyol solution in uniform supply to the resin surface in the column, and
   i. recovering successively from the downstream side of the resin bed
      1. a fraction comprising unhydrogenated sugars and other impurities, and
      2. a second fraction comprising substantially pure polyols.

* * * * *

UNITED STATES PATENT AND TRADEMARK OFFICE
CERTIFICATE OF CORRECTION

PATENT NO. : 4,008,285
DATED : February 15, 1977
INVENTOR(S) : Melaja et al.

It is certified that error appears in the above-identified patent and that said Letters Patent are hereby corrected as shown below:

First page, Col. 2, line 4, "3,830,770" should be --3,730,770--;
Col. 1, line 26, "xyloserich" should read --xylose-rich--;

Col. 1, last line, after "hulls" change the comma to a period;
Col. 2, line 26, "or" should read --of--;
Col. 3, line 38, "Altenatively" should read --Alternatively--;
Col. 4, line 7, after "of" insert --a--;
Col. 4, line 44, "hydrosylate" should read --hydrolysate--;
Col. 4, line 52, "and and" should read --and any--;
Col. 4, line 56, delete "the" (third occurrence);
Col. 4, line 61, "hydrosalate" should read --hydrolysate--;
Col. 5, line 31, after "specifically", delete the comma;
Col. 5, line 33, delete "a";

Col. 7, line 61, "as" should read --is--;
Col. 8, line 4, "the polyol and" should read --a polyol-- and "xylitorl" should read --xylitol--;
Col. 10, line 6, "polystryene" should read --polystyrene--;
Col. 12, line 8, "catio" should read --cation--;
Col. 13, line 1, "the" (first occurrence) should read --an--;
Col. 16, line 16, delete the comma after "$X_1$"; and
Col. 19, line 8, after "balance" insert --of--.

Signed and Sealed this

Twenty-eighth Day of June 1977

[SEAL]

Attest:

RUTH C. MASON
*Attesting Officer*

C. MARSHALL DANN
*Commissioner of Patents and Trademarks*